US009618459B2

(12) United States Patent
Maass

(10) Patent No.: US 9,618,459 B2
(45) Date of Patent: Apr. 11, 2017

(54) SYSTEMS AND METHODS FOR AUTOMATED COMPOSITE LAYUP QUALITY ASSURANCE

(71) Applicant: Flightware, Inc., Guilford, CT (US)

(72) Inventor: David Maass, Guilford, CT (US)

(73) Assignee: Flightware, Inc., Guilford, CT (US)

(*) Notice: Subject to any disclaimer, the term of this patent is extended or adjusted under 35 U.S.C. 154(b) by 0 days.

(21) Appl. No.: 14/851,699

(22) Filed: Sep. 11, 2015

(65) Prior Publication Data

US 2016/0341671 A1    Nov. 24, 2016

Related U.S. Application Data

(60) Provisional application No. 62/163,047, filed on May 18, 2015.

(51) Int. Cl.

| | | |
|---|---|---|
| *G01B 5/28* | (2006.01) | |
| *G01B 5/30* | (2006.01) | |
| *G01N 21/88* | (2006.01) | |
| *B29C 37/00* | (2006.01) | |
| *B29C 70/38* | (2006.01) | |
| *B29K 105/00* | (2006.01) | |

(52) U.S. Cl.
CPC ..... *G01N 21/8851* (2013.01); *B29C 37/0053* (2013.01); *B29C 70/386* (2013.01); *B29C 2037/903* (2013.01); *B29K 2105/253* (2013.01); *G01N 2201/04* (2013.01)

(58) Field of Classification Search
CPC ........... B29C 37/0053; G01N 21/8851; G01N 2201/04

USPC ................................. 702/40, 41, 33, 39, 35
See application file for complete search history.

(56) References Cited

U.S. PATENT DOCUMENTS

| | | | |
|---|---|---|---|
| 5,562,788 A * | 10/1996 | Kitson | B29C 70/384 |
| | | | 156/378 |
| 5,848,115 A | 12/1998 | Little et al. | |
| 6,041,132 A | 3/2000 | Isaacs et al. | |
| 6,799,619 B2 | 10/2004 | Holmes et al. | |
| 6,814,822 B2 | 11/2004 | Holmes et al. | |
| 6,871,684 B2 | 3/2005 | Engelbart et al. | |
| 7,039,485 B2 | 5/2006 | Engelbart et al. | |
| 7,171,033 B2 | 1/2007 | Engelbart et al. | |
| 7,193,696 B2 | 3/2007 | Engelbart et al. | |
| 7,236,625 B2 | 6/2007 | Engelbart et al. | |
| 7,289,656 B2 | 10/2007 | Engelbart et al. | |
| 7,362,427 B2 | 4/2008 | Fayolle et al. | |
| 7,372,556 B2 | 5/2008 | Engelbart et al. | |
| 7,372,558 B2 | 5/2008 | Kaufman et al. | |
| 7,424,902 B2 | 9/2008 | Engelbart et al. | |
| 7,435,947 B2 | 10/2008 | Engelbart et al. | |
| 7,480,037 B2 | 1/2009 | Palmateer et al. | |

(Continued)

OTHER PUBLICATIONS

Automated Ply Inspection (API) for AFP Project ( http://catalog.data.gov/dataset/automated-ply-inspection-api-for-afp-project) Download date Sep. 24, 2015; 4 pps.

(Continued)

*Primary Examiner* — Gregory J Toatley
*Assistant Examiner* — Eman Alkafawi
(74) *Attorney, Agent, or Firm* — Carson C. K. Fincham; Fincham Downs, LLC

(57) ABSTRACT

Systems, methods, apparatus, and articles of manufacture for automated composite layup quality assurance.

24 Claims, 12 Drawing Sheets

(56) References Cited

U.S. PATENT DOCUMENTS

| | | | |
|---|---|---|---|
| 7,489,392 B2 | 2/2009 | Engelbart et al. | |
| 7,513,964 B2 | 4/2009 | Ritter et al. | |
| 7,555,404 B2 | 6/2009 | Brennan et al. | |
| 7,576,850 B2 | 8/2009 | Engelbart et al. | |
| 7,602,963 B2 | 10/2009 | Nightingale et al. | |
| 7,678,214 B2 | 3/2010 | Engelbart et al. | |
| 7,688,434 B2 | 3/2010 | Engelbart et al. | |
| 7,712,502 B2 | 5/2010 | Engelbart et al. | |
| 7,769,224 B2 | 8/2010 | Engelbart et al. | |
| 7,807,002 B2 | 10/2010 | Engelbart et al. | |
| 7,889,907 B2 | 2/2011 | Engelbart et al. | |
| 7,978,328 B2 | 7/2011 | Engelbart et al. | |
| 7,983,469 B2 | 7/2011 | Engelbart et al. | |
| 8,068,659 B2 | 11/2011 | Engelbart et al. | |
| 8,103,085 B1 | 1/2012 | Zadeh | |
| 8,184,281 B2 | 5/2012 | Engelbart et al. | |
| 8,505,181 B1* | 8/2013 | Brostmeyer | F01D 5/005 29/404 |
| 8,780,223 B2 | 7/2014 | Beauchemin | |
| 2004/0189944 A1* | 9/2004 | Kaufman | G03B 31/00 352/10 |
| 2005/0023414 A1 | 2/2005 | Braun | |
| 2005/0203657 A1 | 9/2005 | Engelbart et al. | |
| 2005/0207468 A1 | 9/2005 | McCullough et al. | |
| 2005/0225753 A1 | 10/2005 | Engelbart et al. | |
| 2006/0191622 A1 | 8/2006 | Ritter et al. | |
| 2007/0204555 A1* | 9/2007 | Engelbart | B29C 70/384 52/741.1 |
| 2008/0259325 A1* | 10/2008 | Engelbart | B29C 70/32 356/237.3 |
| 2009/0043533 A1* | 2/2009 | Brennan | B29C 70/32 702/152 |
| 2009/0169056 A1 | 7/2009 | Engelbart et al. | |
| 2009/0199948 A1 | 8/2009 | Kirsch | |
| 2009/0228218 A1 | 9/2009 | Butkiewicz | |
| 2010/0204929 A1 | 8/2010 | Engelbart et al. | |
| 2010/0263505 A1 | 10/2010 | Engelbart et al. | |
| 2011/0290421 A1 | 12/2011 | Santos Gomez | |
| 2012/0216957 A1 | 8/2012 | Engelbart et al. | |
| 2012/0330453 A1 | 12/2012 | Samak Sangari et al. | |
| 2013/0010309 A1 | 1/2013 | Engelbart et al. | |
| 2014/0132729 A1 | 5/2014 | Foulk et al. | |
| 2014/0376800 A1* | 12/2014 | Cooper | G01N 21/8851 382/141 |
| 2015/0015602 A1 | 1/2015 | Beaudoin | |
| 2015/0046098 A1 | 2/2015 | Jack et al. | |
| 2015/0063707 A1 | 3/2015 | Fu | |
| 2015/0078651 A1* | 3/2015 | Lilienblum | G01B 21/20 382/154 |
| 2015/0106062 A1 | 4/2015 | Chen-Keat et al. | |
| 2015/0146964 A1 | 5/2015 | Tai et al. | |
| 2015/0189201 A1* | 7/2015 | Bridges | H04N 5/35554 348/46 |

OTHER PUBLICATIONS

Mitchell "A machine vision system using fast texture analysis for automated visual inspection" Systems Engineering 1992; 4 pps.

Nahangi et al., "Automated assembly discrepancy feedback using 3D imaging and forward kinematics" Automation in Construction; vol. 56, Aug. 2015, 12 pps.

International Search Report for PCT/US15/050339 dated Dec. 4, 2015; 3 pps.

Written Opinion for PCT/US15/050339 dated Dec. 4, 2015; 20 pps.

* cited by examiner

SYSTEMS AND METHODS FOR AUTOMATED COMPOSITE LAYUP QUALITY ASSURANCE

CROSS-REFERENCE TO RELATED APPLICATIONS

The present application claims benefit and priority under 35 U.S.C. §119 to, and is a non-provisional of, U.S. Provisional Patent Application 62/163,047 filed on May 18, 2015 and titled "SYSTEMS AND METHODS FOR AUTOMATED COMPOSITE LAYUP QUALITY ASSURANCE", the contents of which are hereby incorporated by reference herein.

GOVERNMENT LICENSE RIGHTS

This invention was made with government support under contract NNX14CL39P awarded by NASA. The government has certain rights in the invention.

BACKGROUND

Composite materials such as carbon fiber composites are manufactured by depositing layers of "prepreg" on a mold, mandrel, or "tool". This process and the resulting deposit thereof are generally referred to as "layup", as the prepreg materials are "laid up" onto the mold or tool surface. This process is repeated many times to build up the layers, sequences, or plies, of the final composite laminate. Inspection of the layup of material used in the manufacture of composite parts is often an important part of the manufacturing process. Indeed, layup inspection is a requirement in the aerospace industry due to the necessary structural integrity of the composite parts, which relies upon proper layup (i.e., the specific location and sequence of the plies or tapes of material the part is made from). Government (e.g., the Federal Aeronautics Administration (FAA)) and industry requirements call for verification of proper layup using intermediate, in process inspections, whether the layups are created by hand or by automated equipment (e.g., Automated Fiber Placement (AFP)). Currently all layup inspection in the aerospace industry is performed manually.

BRIEF DESCRIPTION OF THE DRAWINGS

An understanding of embodiments described herein and many of the attendant advantages thereof may be readily obtained by reference to the following detailed description when considered with the accompanying drawings, wherein.

DETAILED DESCRIPTION

I. Introduction

Figure 1:
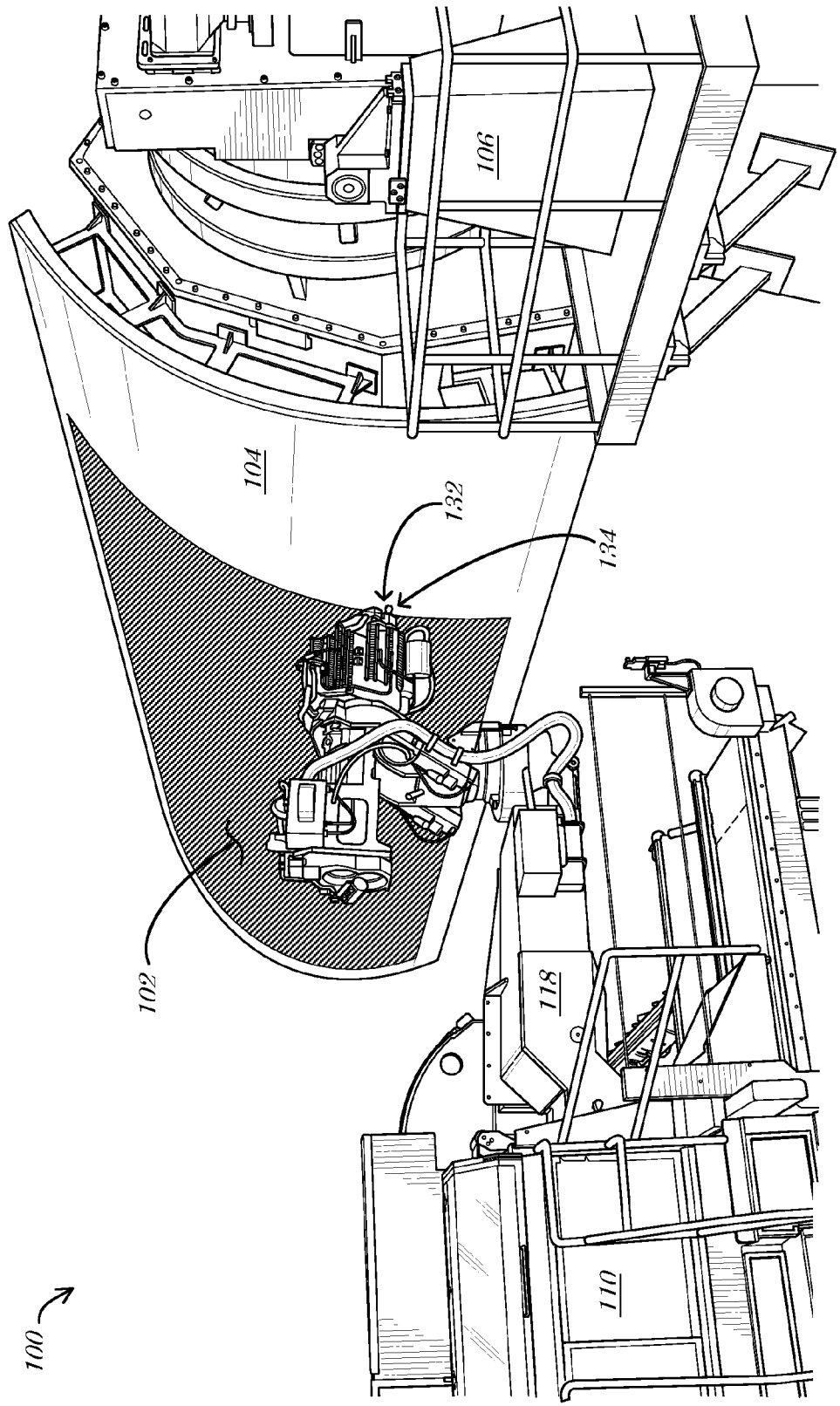
FIG. 1 is a perspective diagram of an Automated Fiber Placement (AFP) system according to some embodiments.

Manual layup inspection is a tedious and difficult task where an inspector relies upon their eyes to perform a complete visual scan of the layup surface to detect all instances of defined layup flaws. For large parts, this is particularly time consuming. For example, to inspect one layup sequence for a Boeing® 787™ fuselage barrel segment requires six (6) Inspectors working for ninety (90) minutes. This is repeated for every ply sequence—for one 787™ fuselage barrel there are sixty-eight (68) ply sequences needed to make the single part. Therefore the layup operation must be interrupted sixty-eight (68) times to perform inspection of every ply, which substantially increases the cycle time of the mold in the layup machine.

Large, complex parts like the 787™ fuselage barrel are often made utilizing Automated Fiber Placement (AFP) equipment, which performs the layup of these parts by placing composite tapes (or "tows") using computer control. After the AFP machine has placed one ply sequence, the machine is idle during manual inspection and any necessary rework is performed. This is inefficient, as expensive capital equipment is dedicated to one part but often is only in use twenty-five percent (25%) to thirty-five percent (35%) of the time. When a flaw is located, the inspector then measures and records the size and location of the flaw, all manually.

In addition to identifying discrete flaws the inspector is responsible for validating that all material has been placed in the proper location on the tool (even if it has no flaws in this region). This task is also difficult and time consuming because tape features such as edges and ends are not easy to detect visually. The composite material utilized by AFP equipment is typically graphite/epoxy "prepreg" (e.g., fiber pre-impregnated with an amount of epoxy or resin), which is a black material with directional reflectance. A black-on-black scene makes it difficult for human inspectors to discern the boundaries between bands and/or tapes.

Furthermore, it is very difficult to know exactly where each layup feature was intended (i.e., programmed) to be located, as there is no reference grid on the layup itself for guidance. In some case, laser pattern projectors are used where the programmed layup features such as tape edges and ends are projected onto the layup surface as green or red laser lines. Even when this is used, the inspector must compare every bright laser line against a much more subtle presentation of the actual tape feature and determine if they match within a defined tolerance dimension.

Should a feature be mislocated, the inspector must measure the mislocated feature, typically using a six (6) inch pocket rule, determine the extent of the mismatch, pinpoint the precise location on the part where the mismatch is present and then record it, all manually. Using the 787™ fuselage as an ongoing example, there are approximately one hundred and seventy-six thousand (176,000) tapes placed in a single part, consisting of about two million (2,000,000) lineal feet, so inspecting the edge and end features of these bands and/or tapes is a large and time consuming task.

Current manual inspection of composite layups is costly and prone to error. It is often a limiting factor for manufacturing productivity, and contributes to low utilization of expensive capital assets. This difficult, relatively boring and time consuming work can often result in errors (undetected flaws, or "escapes"). Manually composed layup flaw records are also difficult to archive and therefore are not conducive to digital analysis which may help to find systematic problems that contribute to flaw generation.

II. AFP Systems

Embodiments presented herein are descriptive of systems, methods, apparatus, and articles of manufacture for automated composite layup quality assurance. An example AFP system 100 according to some embodiments is shown in FIG. 1. The AFP system 100 may comprise, for example, a carbon-fiber layup area 102 deposited on a mold 104. As depicted, the mold 104 may comprise a curved work surface upon which the layup area 102 is defined by deposition of layup tapes, bands, and/or sequences (not distinguishable from the overall layup area 102 in FIG. 1). As utilized herein, the term "sequence" is utilized to refer to a particular layer, level, or "ply" of a composite material, each sequence being defined by a plurality of "courses" or bands laid up onto a mold (e.g., directly, or on top of a previously-laid up sequence), with each course being defined by a plurality of "tapes" or "tows" of composite layup material. The various courses of a sequence are often laid up in parallel strips on the mold, but any particular sequence may include courses laid up in a variety of orientations. In some embodiments, the mold 104 may be held, positioned, and/or moved by one or more mold supports 106. According to some embodiments, the layup tapes, courses, and/or sequences comprising the layup area 102 may be deposited on the mold 104 by in response to commands issued by and/or due to program code executed by a controller 110. The controller 110 may comprise, for example, a specially-programmed computerized device and/or processing device coupled to actuate and/or control an articulating, robotic, and/or otherwise moveable positioning device 118. The positioning device 118 may, in some embodiments, comprise a gantry, tracked, and/or articulating system coupled to direct an AFP head 132. The AFP head 132 may, for example, be mounted to the positioning device 118 such as to reposition and/or direct the AFP head 132 with respect to the mold 104 (the AFP head 132 may, for example, comprise an articulating robotic fiber placement tool), e.g., in response to commands received from the controller 110. In some embodiments, the controller 110 may execute one or more algorithms and/or software procedures to adjust the positioning of the AFP head 132 (e.g., via the positing device 118) and/or the mold 104 (e.g., via actuatable mold supports 106) to affect the depositing of the layup area 102. In some embodiments, a laser line scanner 134 (or other sensor) may be coupled to the AFP head 132 to detect data descriptive of the layup area 102 as individual tapes, courses, and/or sequences are deposited (e.g., in "real-time"). According to some embodiments, the AFP controller 110 (and/or another processing device) may conduct AFP quality assurance data processing as described herein (e.g., with respect to the methods 500, 600, 700, 800 of FIG. 5, FIG. 6, FIG. 7, and/or FIG. 8 herein, and/or portions or combinations thereof.

Software of embodiments described herein, for example, is unique when compared with other known solutions. Embodiments described herein, for example, may enable automation of composite layup inspection. A primary benefit of automated inspection is that it can be performed in much less time. This time saving reduces the overall cycle time to manufacture the composite part (e.g., of which the layup area 102 is a portion of), resulting in higher productivity and lower manufactured unit cost. Automated inspection also reduces labor cost associated with manual inspectors performing this function.

Reduced inspection time for automated manufacturing processes such as AFP can result in higher machine utilization rate. Higher utilization allows the cost of the equipment (e.g., the system 100 and/or components thereof) to be recaptured sooner, meaning that the return on investment for the equipment is improved. In some cases, this may mean that additional work can be accommodated on an existing machine, thereby eliminating the need for an additional machine to provide the needed capacity.

Automating a time consuming, difficult and sometimes boring manual process improves quality and efficacy of the composite material layup inspection process. This can result in fewer missed flaws ("escapes") with a potential to improve safety and reduce product liability costs.

Currently, using manual inspection, flaws are only noted after a complete ply sequence (e.g., a number of tapes and/or courses of fiber material) has been manufactured. If a flaw is created early in the layup sequence, the flaw can be present in a large portion of that layup sequence. This means a large portion of that layup sequence may require subsequent repair, which often requires removal of the flawed material and replacing it. Where automated layup inspection can be performed in real time, cost and time savings can be realized. In such embodiments, layup data collection and processing may be performed at the same time as a machine such as the AFP head 132 creates the layup area 102. Near instantaneous detection of layup flaws when they are created enables the layup machine to be stopped and fixed. This minimizes the amount of flaws created, which in turn minimizes the cost and time necessary to rework or repair such flaws.

Automated layup inspection creates a detailed digital record of the part layup (e.g., a digital representation of the layup area 102), which is valuable in several ways. Critical aerospace parts, such as many of the composite parts that can be inspected in this manner, require detailed manufacturing records in the event that such part may later be involved in service difficulties, incidents or even an accident. These records are used to help determine if anything about the part's original manufacturing process may have contributed to the problem, or can be ruled out as a contributing factor. From an operations perspective, digital records of serialized parts can also be used to determine if specific problems are present in these parts, even long after the parts have left the factory. For example, consistent presence of mislocated tapes and/or courses in a certain region of part may be tied to the introduction of a new part mold (e.g., the mold 104), which contains a discrepant region (not shown). There is recent emphasis in aerospace manufacturing to move towards the "digital thread" (maintaining digital records), and embodiments herein that provide digital layup feature and/or flaw data for automated layup inspection and/or correction provide an advance in reaching the digital thread goal.

Applicant has realized that it is desirable to have a process that automates the inspection of composite layups that allows for the detection of layup features and flaws from sensor data. In addition, it is desirable to have a process that can separate and classify or categorize detected features according to a multitude of feature and/or flaw types. Furthermore, it is also desirable to have a process that determines precise locations and dimensions of these features and/or flaws. Still further, it is desirable to have a method where the feature and/or flaw dimensions and location can be used to automatically disposition detected features and/or flaws (accept, repair or reject) in accordance with specifications that are based on flaw type, dimensions and location. It is also desirable to have a process where detected feature and/or flaw information is in a format where it can be displayed directly on the composite layup area 102 using methods such as laser projection (not shown in FIG. 1) to assist an operator (also not shown) to locate and repair detected flaws. While there has been some effort to address the various issues of automating composite layup quality assurance, the algorithms and procedures necessary to provide automation of layup inspection are not readily apparent from the manual inspection process and little or no attention has been paid to the particular software algorithms that may be utilized to achieve these and other desired advantages. Therefore, there currently exists a need in the industry for a process that automates the inspection of composite layups such as by detecting and/or identifying layup features and/or flaws from sensor data.

Automated inspection of composite layups poses numerous challenges, many which are not obvious at first glance. The prepreg material being inspected is in an uncured, pliable state which means that dimensional features such as the edges or ends of the prepreg tape are not firmly defined, as they would be if the material was in a final, cured, rigid state. This suggests a noncontact inspection method. Other and/or additional challenges may be more easily understood with reference to FIG. 2, in which a perspective diagram of a portion of an example composite material layup ply sequence 202 according to some embodiments is shown.

Figure 2:
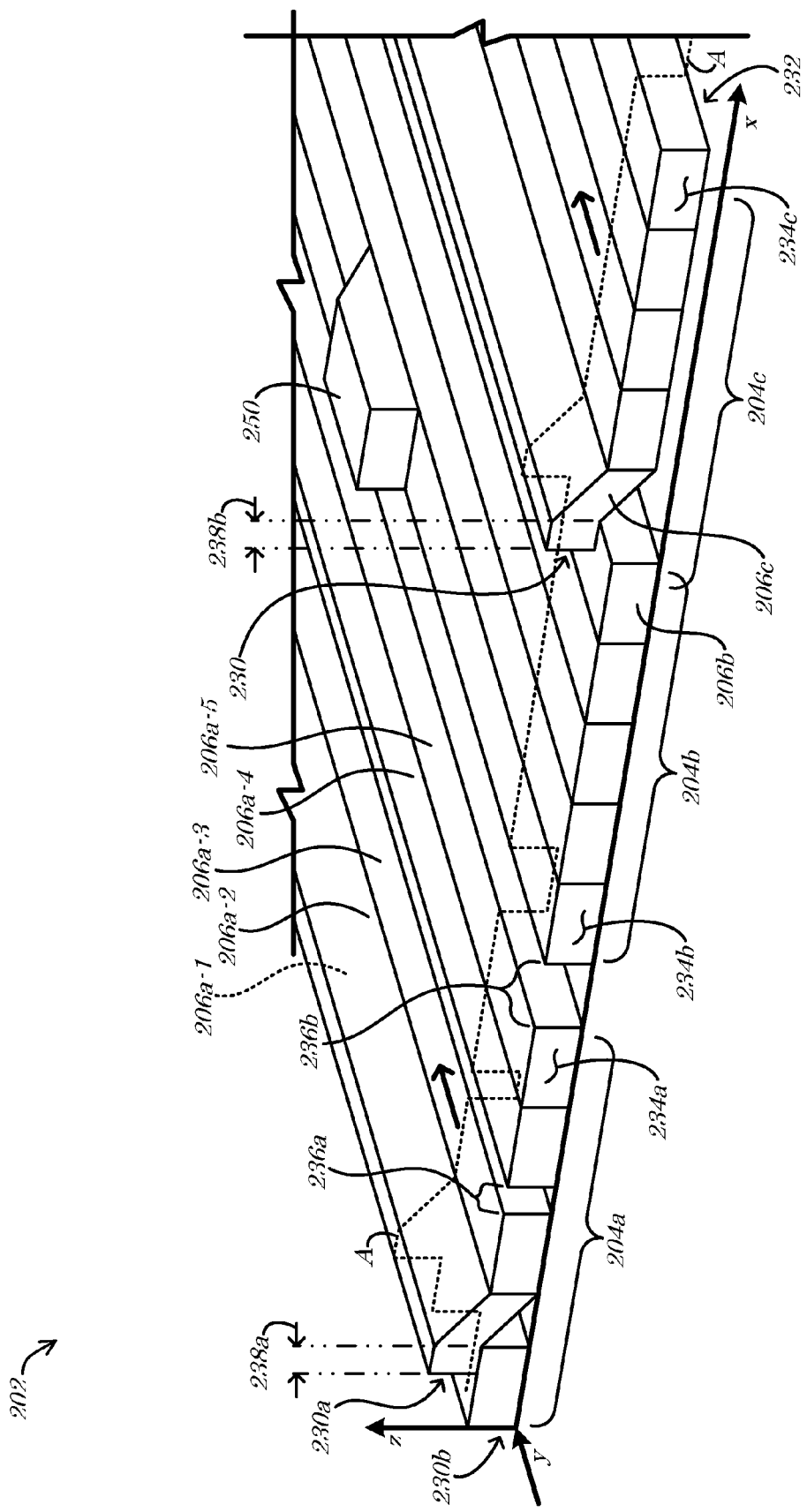
FIG. 2 is a perspective diagram of a portion of an example composite material layup ply sequence according to some embodiments.

The depicted portion of the layup ply sequence 202 may comprise, for example, a plurality of composite material or prepreg courses (or bands) 204*a-c*, such as a first course 204*a*, a second course 204*b*, and a third course 204*c* as depicted for purposes of non-limiting example in FIG. 2. In some embodiments, each course 204*a-c* may comprise a plurality of "tows" or tapes 206*a-c*, e.g., individual bundles or strands of carbon-fiber prepreg laid up together to form each respective course 204*a-c*. As depicted in FIG. 2 and as utilized for continuing reference in the examples described herein, the layup ply sequence 202 may be referenced in a three-dimensional (3-D) coordinate plane comprising an x-axis extending laterally through the layup ply sequence 202, a y-axis extending along the layup ply sequence 202, and a z-axis disposed normally to the layup ply sequence 202. In such an arrangement, the number of tapes 206*a-c* and/or courses 204*a-c* may be indexed with reference to an x-datum, a length of the layup ply sequence 202 (and/or individual tapes 206*a-c* and/or courses 204*a-c* thereof) may be indexed with reference to a y-datum, and a height or thickness of the layup ply sequence 202 (and/or tapes 206*a-c* and/or courses 204*a-c* thereof) may be indexed with reference to a z-datum. In some embodiments, the x, y, and z-axis orientation depicted in FIG. 2 for ease of description and/or as utilized to perform automated fiber placement quality assurance as described herein, may differ from a coordinate system utilized to define and/or locate an underlying mold, tool, and/or part (none of which are shown in FIG. 2).

In accordance with some embodiments, a scan line "A" may be disposed along the x-axis (i.e., perpendicular to the y-axis) at a particular starting location (i.e., a starting y-coordinate; not shown) and progress along the length of the layup ply sequence 202, with subsequent scan line "A" locations being represented by subsequent and/or consecutive y-coordinates (the progression of which is depicted by bold arrows in FIG. 2). As utilized herein, the term "scan line" refers to a line along the x-axis (i.e., each point on the line having the same y-coordinate) and the terms "scan axis line" and/or "axis line" refer to a line along the y-axis (i.e., each point on the line having the same x-coordinate).

According to some embodiments, the scan data may be utilized (as described in detail herein) to identify various features and/or flaws of the layup ply sequence 202. Such features may include, for example, a course 204*c* left or first edge 230*a-b* (e.g., at or near the x-datum), a right or second edge 232 (e.g., located at some x-coordinate greater than that of the first edge 230*a-b*), an end 234*a-c* (e.g., a first end, in some embodiments, such as in the case a second end (not shown) is located at an opposing end of the layup ply sequence 202), a gap 236*a-b*, and/or an overlap 238*a-b*. As depicted in FIG. 2, in some embodiments a left edge 230*a-b* may comprise one or more of a left tape edge 230*a* and/or a left course edge 230*b*. According to some embodiments, the left tape edge 230*a* may be coincident with and/or define the left course edge 230*b* (not the situation shown in FIG. 2 with respect to a second tape 206*a*-2 of a first course 204*a*).

In some embodiments, as depicted in FIG. 2, two or more of the courses 204*a-c* may comprise ends 234*a-c* having different y-coordinate positions. A first end 234*a* of the first course 204*a* may be disposed at a first y-coordinate, for example, while a second end 234*b* of a second course 204*b* and/or a third end 234*c* of a third course 204*c* may be disposed at second and third y-coordinates, respectively. As depicted, in some embodiments the gap 236*a-b* may comprise a tape gap 236*a* occurring between an adjacent third tape 206*a*-3 and a fourth tape 206*a*-4 and/or may comprise a course gap 236*b* occurring between the first course 204*a* and the second course 204*b*. According to some embodiments, the overlap 238*a-b* may be defined in the case that two adjacent tapes 206*a*-1, 206*a*-2, 206*b*, 206*c* and/or two adjacent courses 204*b*, 204-*c* become at least partially stacked on top of one another. As depicted for purposes of example in FIG. 2, a first tape 206*a*-1 of the first course 204*a* may be overlapped by the second tape 206*a*-2 and/or a tape 206*b*-5 of the second course 204*b* may be overlapped by a tape 206*c*-1 of the third course 204*c*, for at least a portion of the length of the layup ply sequence 202. While uniform gaps 236*a-b* and overlaps 238*a-b* are depicted for ease of illustration in FIG. 2, it should be understood that variances in these features (lengths, thicknesses, extent of overlapping, etc.) may occur in practice.

In some embodiments, the scan data may be utilized (as described in detail herein) to identify other and/or additional features and/or flaws of the layup ply sequence 202 such as, but not limited to, a splice 250, and/or: a bridge, twist, buckle, "fuzz" ball, and/or foreign matter (none of which are depicted in FIG. 2). These generally apply to a single tape 206*a-c* or group of tapes in a single course 204*a-c*, or within a group of courses. The splice 250 may, for example, comprise a portion of one or more tapes 206*a-c*. Splices 250 are joints between two shorter tapes that are located within a single tape supply roll in order that each roll have the same total length. The splice 250 may be identified at least in part due to a respectively (and/or relatively) short length, e.g., of the overlap in the direction of the tape.

The prepreg materials (e.g., the tapes 206a-c) commonly used in the aerospace industry are on the order of one hundred and twenty-five (125) microns (five thousandths (0.005) of an inch) thick, which means that any measurement system (or sensor) to be employed (e.g., in effectuating the scan line "A") should, in some embodiments, be capable of thickness measurement resolution, accuracy and precision considerably less than one hundred and twenty-five (125) microns, on the order of twenty-five (25) microns (one thousandth (0.001) of an inch) or less, to be able to distinguish one tape 206a-c and/or course 204a-c from an overlapping tape 206a-c and/or course 204a-c. However, layup areas (e.g., the layup ply sequence 202) inspected may extend up to five hundred (500) inches in width or length. It is challenging to find an inspection method that covers an inspection volume of this size, with the level of the resolution, accuracy and thickness precision needed.

According to some embodiments, the sensor system (e.g., the AFP system 100 of FIG. 1) used may be able to measure the layup ply sequence 202 with a very large number of measurement locations (high areal density) over the layup area (e.g., the layup area 102 of FIG. 1). The defined tolerances for layup feature locations are generally on the order of three hundredths (0.030) of an inch, which means that data should, in some embodiments, be generated at point spacing on the order five thousandths (0.005) of an inch or so to define point locations with sufficient desired accuracy. A grid of points at five thousandths (0.005) of an inch spacing contains forty thousand (40,000) points per square inch, or about two and three tenths of a billion (2.3 B) points for a layup that may be forty (40) feet by ten (10) feet in area.

In order to perform measurements in a reasonable time, the sensor system may, in accordance with some embodiments, acquire data at a very high rate. For example, a single sequence or ply layup that is forty (40) foot by ten (10) foot in the example above can be created by an AFP machine in as little as thirty (30) minutes. To achieve an inspection time of fifteen (15) minutes (to be economically feasible) requires that the two and three tenths of a billion (2.3 B) measurement points be collected at the rate of about two and one half million (2.5 M) points per second (2.5 M/sec).

One methodology that meets these criteria is laser line scanning or profilometry. A laser line scanner or sensor comprises a laser line generator and a camera set at a defined angle to each other. Using trigonometry, the image of the laser line can be converted to a series of discrete point locations along the line (e.g., the scan line "A"), where the height (z) and distance (x) along the line can be very accurately derived. A typical sensor measures a line about four (4) inches wide at one thousand (1,000) to one thousand five hundred (1,500) point locations. Furthermore, laser line scanners can operate at sampling (measurement) rates as high as sixty-four thousand (64,000) lines per second.

While laser line scanners appear to provide the capabilities needed, many of the practical limitations of their use in this application are not at all obvious. A laser line scanner or sensor uses an image and therefore has some of the same limitations of image based systems. Composite prepreg materials are specular (directionally reflective) and offer low contrast. This means that the laser line scanner must be oriented very close to normal to the layup surface. The sensor has a depth of field limitation, and the combination of surface near-normality and sensor height above the surface can result in a collision between the sensor and the Layup in certain regions. This is particularly a problem for a laser line sensor mounted directly on the AFP machine head, to perform real-time inspection during layup.

Because the prepreg surface is not even or uniform, there are portions of the laser line that are not fully reflected and therefore cannot be detected by the camera. This means that many or most lines of measurements contain missing points (from a single point to hundreds of points). In addition the laser data contains characteristic noise that can be a considerable fraction of the ply thickness. The noise and irregularity of missing measurement points makes evaluating and interpreting these points as specific layup features to a desired degree of reliability much more difficult than is apparent at the conceptual level.

Figure 3:
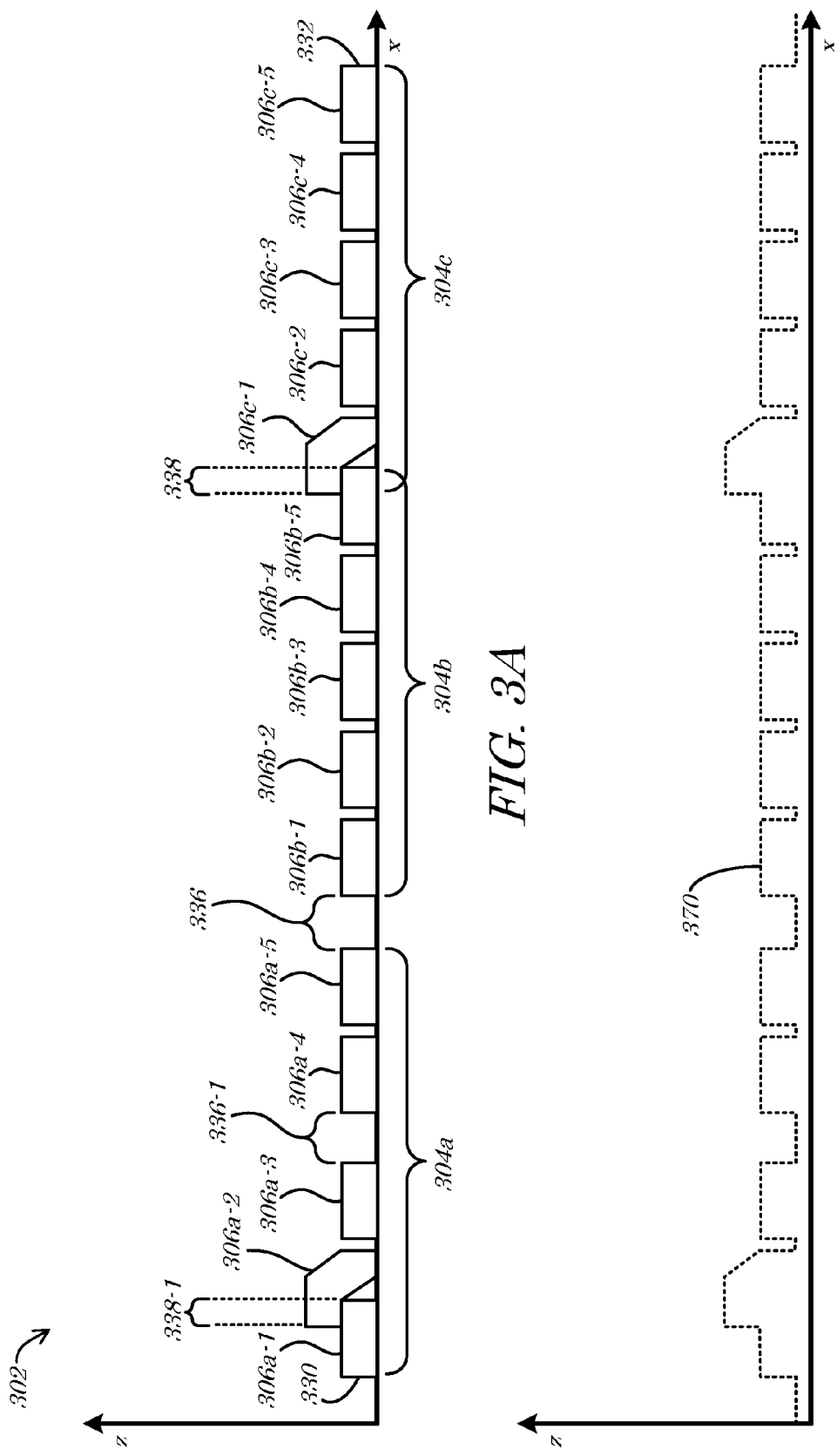
FIG. 3A is an end view of an example composite material layup ply sequence according to some embodiments.
FIG. 3B is graph of expected results from a scan of the example composite material layup ply sequence of FIG. 3A.

As depicted in FIG. 3A, for example, an end view of an example composite material layup ply sequence 302 according to some embodiments is shown. In some embodiments, the layup ply sequence 302 may be similar to the layup ply sequence 202 of FIG. 2, representing an ongoing example provided for illustration of the novel concepts herein. The layup ply sequence 302 may comprise, for example, three (3) courses 304a-c, each course 304a-c comprising five (5) tapes 306a-c. A first course 304a may comprise a first set of five tapes 306a-1, 306a-2, 306a-3, 306a-4, 306a-5, for example, and/or a second course 304b may comprise a second set of five tapes 306b-1, 306b-2, 306b-3, 306b-4, 306b-5 and/or third course 304c may comprise a third set of five tapes 306c-1, 306c-2, 306c-3, 306c-4, 306c-5. In some embodiments, as depicted, the first course 304a (and/or the first tape 306a-1 thereof) may define a left edge 330 of the material layup ply sequence 302 and/or the third course 304c (and/or the fifth tape 306c-5 thereof) may define a right edge 332 of the material layup ply sequence 302. In some embodiments, left and/or right edges of individual tapes 306a-c that are not coincident with edges of courses 304a-c may be identified (not separately labeled in FIG. 3A). According to some embodiments, there may be a gap 336 between the first course 304a (and/or the fifth tape 306a-5 thereof) and the second course 304b (and/or the first tape 306b-1 thereof). In some embodiments, a tape gap 336-1 may occur between various tapes 306a-c, such as the tape gap 336-1 explicitly depicted and labeled between the third tape 306a-3 and the fourth tape 306a-4 of the first course 304a. According to some embodiments, an overlap 338 may exist between the second course 304b (and/or the fifth tape 306b-5 thereof) and the third course 304c (and/or the first tape 306c-1 thereof). In some embodiments, a tape overlap 338-1 may occur between various tapes 306a-c, such as the tape gap 338-1 explicitly depicted and labeled between the first tape 306a-1 and the second tape 306a-2 of the first course 304a.

In theory, the surface profile (height measurement of the top or upper surface of the layup ply sequence 302) should appear as depicted by the results 370 in FIG. 3B. In theory, each tape 306a-c has a flat surface at the same height as its neighbor within its respective course 304a-c, or within the overall layup ply sequence 302. In theory, there may be a small gap 336-1 between adjacent tapes 306a-c (e.g., between the third tape 306a-3 and the fourth tape 306a-4 as explicitly depicted and labeled in FIG. 2), and/or the gaps 336, 336-1 and/or overlaps 338, 338-1 between adjacent courses 304a-c and/or adjacent tapes 306a-c. In the gap 336, 336-1 and/or overlap 338, 338-1 regions, the height difference should be equal to one ply thickness.

Figure 4:
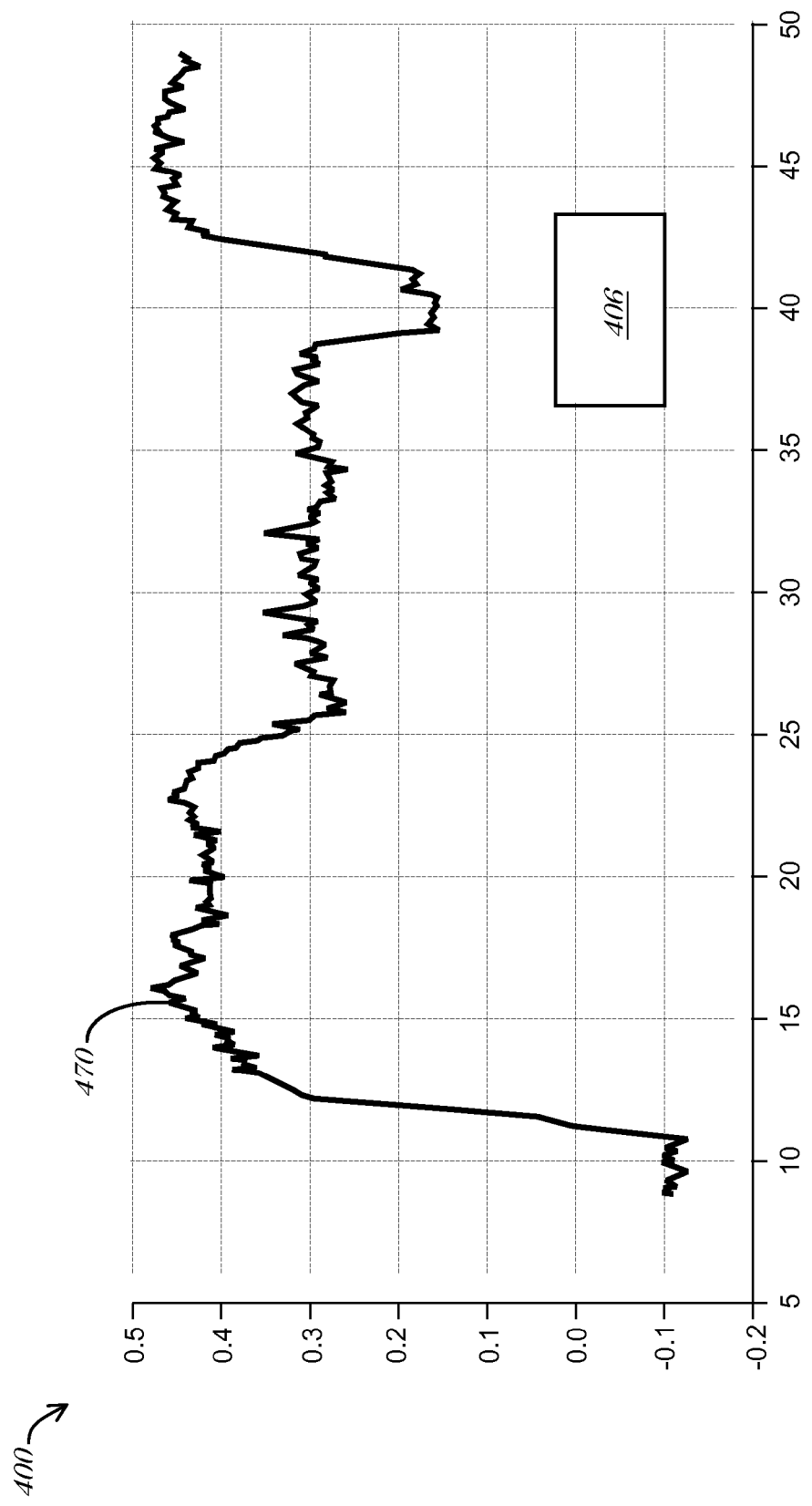
FIG. 4 is graph of example results from a scan of an example composite material layup ply sequence according to some embodiments.

In reality however, typical laser line sensor outputs are quite different from theory (i.e. what one might consider obvious). With reference to FIG. 4, for example, a graph of example results 470 (e.g., laser line scanning results) from a scan of an example composite material layup ply sequence (not shown) according to some embodiments is shown. For reference, the thickness and width of the actual scanned tape 404 is depicted with the results 470. It is clear that the edges of the tapes (or courses) are not at all obvious from this data. In fact, very carefully developed algorithms are needed to reliably extract this information from real measurement data (e.g., from the results 470).

III. Automated Composite Layup Quality Assurance

Embodiments herein are generally descriptive of a computerized process that is specially-programmed to determine composite layup features and flaws from scan data such as three-dimensional (3-D) point cloud data. Features and flaws of composite layup surfaces may be detected, classified and/or categorized, and located in a three-dimensional (3-D) point system, for example, and/or such data may be utilized to facilitate and/or undertake remedial action with respect to identified/located flaws (e.g., the software may be utilized to effectuate movement of an AFP head and/or associated robotic or otherwise actuatable mechanical positing system).

Figure 5:
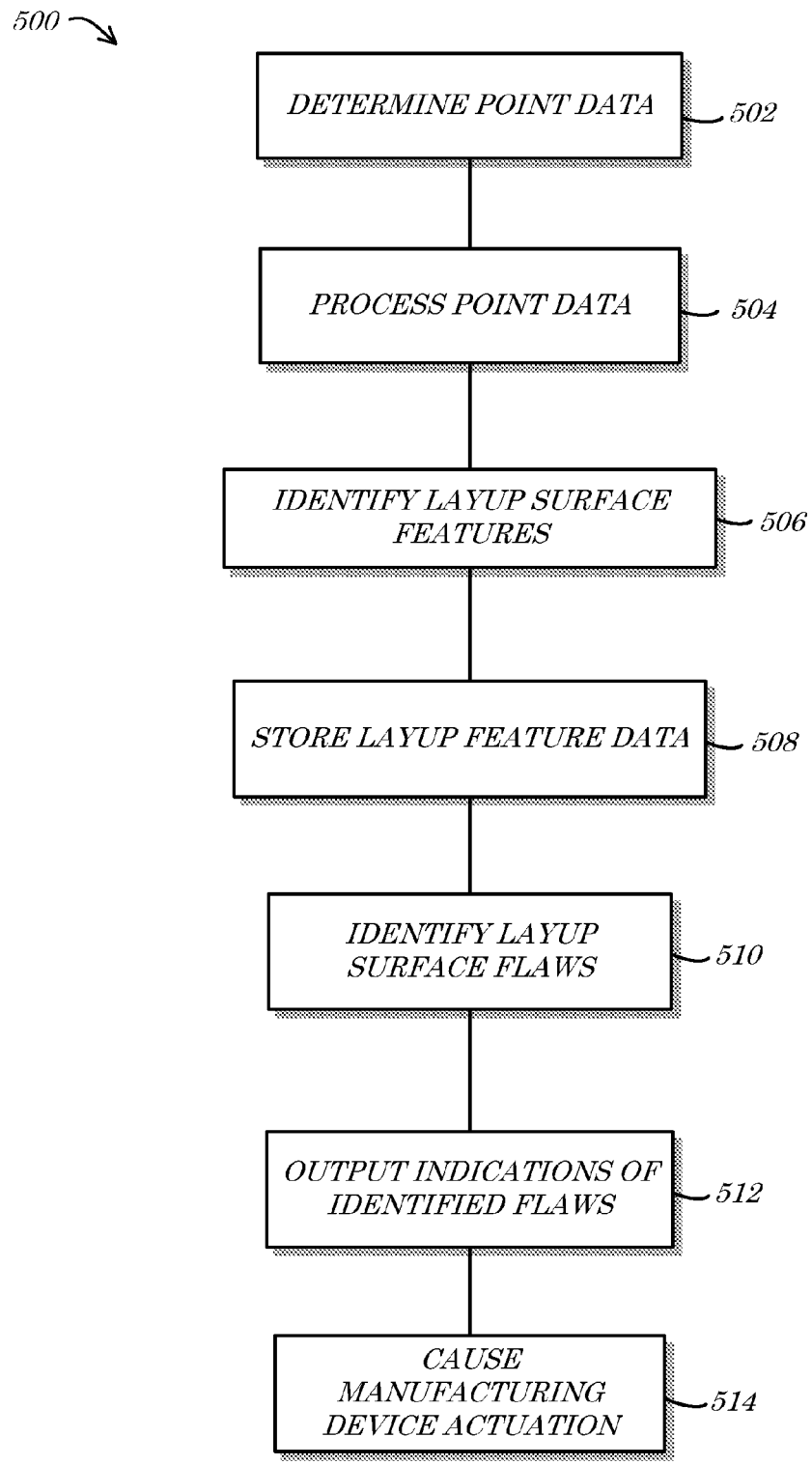
FIG. 5 is a flow diagram of a method according to some embodiments.

Turning now to FIG. 5, for example, a flow diagram of a method 500 according to some embodiments is shown. In some embodiments, the method 500 may comprise an automated composite layup quality assurance method that provides one or more of the advantages described herein and/or that provides other beneficial results. In some embodiments, the method 500 may be performed and/or implemented by and/or otherwise associated with one or more specialized and/or specially-programmed computers (e.g., an AFP controller device), computer terminals, computer servers, computer systems and/or networks, and/or any combinations thereof (e.g., by one or more data processing, manufacturing process, and/or third-party data analysis computers).

The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure. Any of the processes and methods described herein may be performed and/or facilitated by hardware, software (including microcode), firmware, or any combination thereof. For example, a storage medium (e.g., a hard disk, Random Access Memory (RAM) device, cache memory device, Universal Serial Bus (USB) mass storage device, and/or Digital Video Disk (DVD); e.g., the data storage devices 940, 1040*a-e* of FIG. 9, FIG. 10A, FIG. 10B, FIG. 10C, FIG. 10D, and/or FIG. 10E herein) may store thereon instructions that when executed by a machine (such as a computerized processor) result in performance according to any one or more of the embodiments described herein.

In some embodiments, the method 500 may comprise determining (e.g., measuring) point data, at 502. Point cloud data may, for example, comprise two-dimensional (2-D) and/or three-dimensional (3-D) point data descriptive of a scan of a composite layup surface. In the case of real-time scanning, the point data (or a subset of point data) may be received from a scanner device and/or sensor and/or read from a data store (e.g., cache, RAM, a hard-drive) in which point data acquired from a scanner/sensor is stored. In some embodiments, the point data for a particular scan line or instance may be specifically looked up and/or retrieved from a database. One or more portions of available point data may, for example, be loaded into memory (e.g., RAM) for processing and/or analysis, with subsequent and/or additional portions being retrieved and/or loaded at a later processing stage. In some embodiments, the point data acquired by a scanning of the layup surface may be received as input into one or more data processing and/or analysis modules and/or procedures. In some embodiments, the point data may be acquired and/or received from one or more of a laser line scanner, a white light scanner, and a blue light scanner.

As described herein, the spacing between points in the point data (e.g., the "point cloud") and/or the measurement accuracy may, in some embodiments, be sufficiently small to present the layup features and/or flaws of interest to the necessary resolution (e.g., a typical point spacing in the plane of the layup (i.e., the x-y plane) may be seventy-five (75) microns, or about three thousandths (0.003) of an inch between points). According to some embodiments, as features desired for identification in the plane of the layup may typically be on the order of three hundredths of an inch (0.03") in size, the x-direction point spacing may be set at five thousandths of an inch or less (<=0.005"). While a similar resolution may be desired in the y-direction, as measurements in the y-direction are predominately a function of scan rate and sensor travel speed, in cases where these parameters cannot be reasonably set to achieve the desired five thousandths of an inch or less (<=0.005") resolution, the y-direction resolution may alternatively be set to ten thousandths of an inch or less (<=0.010"). In some embodiments, other spacing may be utilized. The resolution and accuracy of the out-of-plane dimension (i.e., the z-dimension) may also or alternatively, in some embodiments, be considerably less than the thickness of one ply or layer of the composite material used in the layup. A typical ply thickness is five thousandths (0.005) of an inch, in which case the desired z-resolution for each of the data points of the point cloud may accordingly be less than about two thousandths (0.002) of an inch), or more preferably, at one thousandth of an inch or less (<=0.001").

In some embodiments, the point data is comprised of data descriptive of a series of "roughly"[1] parallel lines, where the lines span across the laid up courses (also called bands) to be inspected. Each line may comprise a multitude of points across the tapes, at roughly uniform spacing. The lines may be positioned in a path that covers the region of material to be inspected (e.g., the layup area 102 of FIG. 1), following a similar path to the machine that placed (or is currently placing, for real-time analysis) that material onto the surface of the mold and/or part. The spacing between points on an individual line, and between adjacent lines, may generally be sufficiently small to capture the layup features of interest to the necessary resolution.

[1] "roughly" parallel is a term that is descriptive of the fact that in the case of a curved (i.e., non-linear) course of material, scan lines effectuated along a radius of the curve may not be truly parallel. For some AFP machines, for example, the left and right edges of a single curved course may differ by between plus and minus seventeen and twenty-nine percent (17-29%) compared to the distance along the centerline of the course of material. Accordingly, in some embodiments, "roughly" parallel is descriptive of two lines having spacing there between that varies by less than or equal to plus and minus twenty-nine percent (29%).

According to some embodiments, the method 500 may comprise processing the point data, at 504. While the resolution of the point data may be designed to enhance the ability to detect features and/or flaws of specific expected sizes or ranges of size, for example, as described herein, the available point data from one or more scans may be missing a plurality of points. In such cases and in accordance with some embodiments, missing data may be interpolated to fill in gaps in the point data. According to some embodiments, the point data may also or alternatively be interpolated to align some or all of the point data to a standardized spacing or grid/coordinate system. While the scanner may measure the layup surface at set intervals of time and at a set travel speed, for example, variations in the layup surface and/or curvature or other non-uniform surface features may cause recorded data points to be located at varying and/or non-uniform spacing intervals. In such cases, and in accordance with some embodiments, even if point data is not missing, one or more points of the point data may be interpolated to identify derived point data coincident with uniform spacing intervals and/or coordinates, and/or point data at non-uniform intervals and/or coordinates may be ignored or deleted.

In some embodiments, the point data may be adjusted to account for other variations such as to re-orient data descriptive of a layup sequence laid at an angle with respect to a coordinate system. Re-orientation may, for example, facilitate more simplistic, faster, and/or more accurate results from data analysis processing algorithms intended to operate on the point data. In some embodiments, the point data may be transposed and/or translated from a first coordinate system, such as a coordinate system utilized to reference the mold or part (e.g., a coordinate system utilized by a Computer-Aided Design (CAD) and/or Computer-Added Manufacturing (CAM) machine or controller; e.g., the controller 110 of FIG. 1) to a second coordinate system utilized to provide input into various quality assurance algorithms as described herein. According to some embodiments, the point data (or a portion thereof) may be smoothed and/or filtered. The point data may be adjusted with one or more mathematical algorithms, for example, to reduce noise from the scan and/or to otherwise reduce or filter outliers and generally provide a more uniform data set. In some embodiments, the point data may be smoothed in one or more coordinate directions. The point data may be smoothed in the direction of the scan line (e.g., the x-direction), for example, and/or in the direction of the scan (e.g., the y-direction).

According to some embodiments, various parameters descriptive of the layup surface and/or sequence may be determined. Various parameters may be received, looked up, retrieved from memory, retrieved from the point data, and/or derived from the point data. Such parameters may include, for example, tape width, number of tapes per course (or band), number of scan lines to drop at beginning and end of each scan, course (or band) centerline search tolerance, slope threshold for tape edge detection, slope threshold for tape end detection, extra width for searching (beyond nominal course/band width), number of scan lines for averaging, number of points along scan line for averaging, minimum number of peaks required to be considered valid fit, minimum line fit correlation value (and/or variance threshold), and/or maximum splice length. According to some embodiments, one or more of the parameters, such as tape width and/or the number of tapes per course, may be utilized to calculate and/or derive other parameters, such as a centerline of a tape or course.

In some embodiments, the method 500 may comprise detecting or identifying layup surface features, at 506. The method 500 may, for example, detect the presence and/or locations of layup features and/or flaws including, but not limited to tape edges, tape start and end locations, gaps, overlaps and splices between tapes, twisted tapes, buckled tapes, bridged tapes, foreign matter on the tape surface and other flaws. According to some embodiments, each feature and/or flaw is detected and located using a specific algorithm that operates on the three-dimensional (3-D) point data to determine whether the feature and/or flaw is present in a particular region of the point data (e.g., represented and/or described by a subset of point data, such as particular one or more specific scan lines) that is under evaluation. By progressively employing one or more algorithms over the entire point data set, the presence and location of all features and/or flaws of any particular type may be found for an entire layup surface (e.g., the layup surface 102 of FIG. 1).

According to some embodiments, each layup feature type may be detected using an algorithm operating on the point data to identify the presence and location of that feature type. Layup features such as the boundaries of the tapes that comprise the layup (edges, start and end points of each tape and/or tape splices) may be identified and located, for example, by algorithms for each feature type. Manufacturing flaws (such as fuzz balls, twisted tape, bridged tape, foreign contaminants, etc.) may also or alternatively be detected and/or located from the point data using specific algorithms.

In some embodiments, the method 500 may comprise storing layup feature data, at 508. In the case a specific feature and/or flaw is detected, for example, its presence and location may be stored in a file created for the specific layup under examination (e.g., called the feature file).

According to some embodiments, the method 500 may comprise identifying layup surface flaws, such as by evaluating identified features, at 510. Identified features of the layup surface may be compared to one or more predefined and/or pre-stored thresholds, for example, to determine whether a particular feature (or portion thereof) should be classified as a flaw (e.g., a feature having characteristics that fall outside of predetermined desirable parameter value ranges). In some embodiments, the identified features of the layup surface may also or alternatively be compared to predefined and/or pre-stored location data to determine of any particular identified feature (or portion thereof) is appropriately located. While a tape edge may not generally qualify as a "flaw" with respect to predetermined characteristic tolerances (e.g., may be appropriately formed), for example, in the case that the tape edge is not properly disposed at the correct location on the mold or part, the positioning may be identified as a flaw. To create an AFP layup, programmed features such as tape edges and tape ends are generally defined by a Computer Numerical Control (CNC) program that is written to provide instructions to the AFP machine. These machine instructions are written using software that stores and portrays the layup creation in a digital file, and this software can simulate the AFP layup digitally. The as-programmed layup definition is stored in a program file. For example, commercial software that performs this ply layup simulation include Virtual Composite Ply (VCP) offered by the firm CGTech™ of Irvine, Calif., and Advanced Composites Environment Suite (ACES) offered by FivesCincinnati in Hebron, Ky. Specific AFP instructions are stored in digital files such as "VCP files", in the case that VCP software is utilized.

In some embodiments, as-manufactured layup features such as tape edges, beginnings, ends, splices, gaps, and/or overlaps can be digitally evaluated, for purposes of Quality Assurance inspection, directly against their intended (i.e., programmed) locations. Location analysis software in accordance with some embodiments may compare the as-programmed location of each layup feature (for example, a specific edge of a specific tape and/or course) in the program file with the actual (or as-made) location of that feature as recorded in the feature file, e.g., at 508 of FIG. 5. The distance between the as-programmed feature and the as-made feature can be calculated and represents that feature's mislocation or error. If the error/deviation for a feature exceeds the maximum allowed amount (the feature tolerance), the feature location may be defined as a flaw and the flaw type and location are stored in a flaw file. If the location error is less than or equal to the tolerance, the feature may be ignored (i.e. considered unflawed, or acceptable).

According to some embodiments, data descriptive of features identified as flaws may be recorded and/or stored in a flaw file (e.g., a digital data file). Such a flaw file may be useful for inspection, to provide rework information to operators and to archive the as-manufactured details of safety critical composite parts (so called "digital thread"). According to some embodiments, a magnitude of deviance of a feature from desired tolerances (e.g., a magnitude or classification of a flaw) may be utilized to determine an appropriate action with respect to a particular feature. Features that deviate from desired levels but are within a given threshold, for example, may be classified and/or categorized as "accept", while deviations exceeding a first threshold and/or by a first amount may be classified as "fix" (e.g., capable of being repaired, reworked, and/or remediated—e.g., within time and/or budgetary constraints), and/or deviations exceeding a second threshold and/or by a second amount greater than the first amount may be classified as "reject" (e.g., not fixable; must be removed and redone). The evaluation of features to identify and locate flaws may be repeated for each sequence of a layup ply and/or area. According to some embodiments, a flaw file may be created for each layup sequence, ply, and/or layer, e.g., resulting in a plurality of flaw files for a given manufactured composite material part.

In some embodiments, the method 500 may comprise outputting an indication of identified flaws, at 512. The flaws in the flaw file can be displayed, for example, either on a computer screen or projected onto the layup itself directly using a laser projector. This enables the operator to locate the flaws directly on the layup and to repair them as required. In some embodiments, the flaw data may be transmitted electronically via a network, such as to one or more machines or devices utilized in flaw repair or reworking. Data descriptive of flaw types, sizes, locations, and/or other flaw characteristics may, for example, be transmitted to an AFP controller and/or head to assist in and/or effectuate a removal, repair, and/or reworking of one or more flaws. The method 500 may comprise, for example, causing a layup manufacturing device to actuate, at 514, when discrepant material has been removed and needs to be replaced. In some embodiments, such as in the case of real-time flaw identification, an AFP machine may be actuated to become paused, stopped, and/or repositioned based on real-time flaw data (e.g., to correct AFP head placement to reduce or minimize a currently-occurring flaw such as a tape gap or overlap)—thereby effectuating a change in operation of the machine placing the physical composite fibers on the layup mold.

Figure 6:
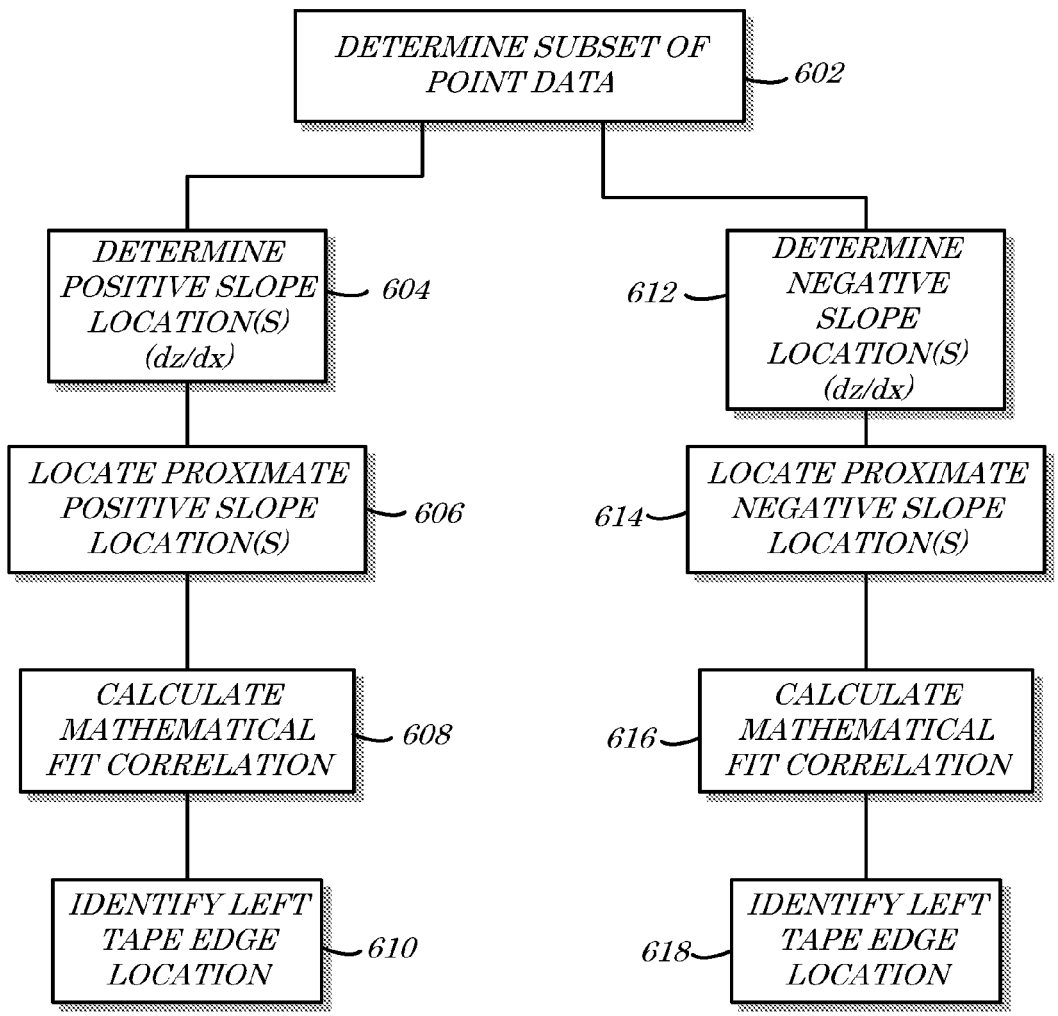
FIG. 6 is a flow diagram of a method according to some embodiments.

According to some embodiments, portions of the method 500 may involve detailed computerized processing such as may be programmed into one or more distinct software modules or procedures. With reference to FIG. 6, for example, a flow diagram of a method 600 according to some embodiments is shown. In some embodiments, the method 600 may comprise a portion of the method 500 such as one or more of the detecting of the layup surface features at 506, the storing of the layup feature data at 508, the evaluating of the identified features at 510, and/or portions or combinations thereof. The method 600 may comprise, for example, a method of detecting, identifying, and/or locating composite layup tape and/or course edges (e.g., "left" edge points and "right" edge points—the left edge having the lowest x-coordinate for an individual tape in a particular scan line and the right edge having the highest x-coordinate for the same tape in the particular scan line).

In some embodiments, the method 600 may comprise determining a subset of available point data, at 602. The available point data may comprise, for example, the point data processed at 504 by the method 500. Interpolated, smoothed, transposed, and/or re-oriented point data descriptive of a layup surface may be received and/or acquired as input into a specially-programmed procedure and/or module for identifying tape and/or course edges, for example. According to some embodiments, the processed point data may comprise data that has been smoothed in the y-direction (i.e., in the direction of movement of the scan sensor across the layup area). In some embodiments, a predetermined number and/or percentage of scan lines and/or points may be skipped over, with the remaining scan line and/or point data defining the determined, selected, and/or identified subset of point data to be utilized for layup feature detection. The number of scan lines and/or points to skip may be predetermined based on a layup parameter determined at the determining of the point data at 502, for example, and/or may be derived based on parameters descriptive of the layup sequence and/or associated scanning process. In some embodiments, a number of scan lines and/or points may be skipped at either or both of the beginning of the point data (e.g., data descriptive of initial surface scanning) and the end of the point data (e.g., data descriptive of final surface scanning). In some embodiments, the point data may be truncated to define the subset of available point data to be utilized for feature location.

According to some embodiments, the method 600 may comprise determining positive slope locations, at 604. For each scan line (i.e., along the x-axis) represented by the subset of available point data, for example, positive slope locations (dz/dx) may be identified. In some embodiments, slope locations having slope values above a predefined positive slope threshold may be recorded as positive slope peak locations (x).

In some embodiments, the method 600 may comprise locating proximate positive slope peak locations, at 606. Over a group of lines before and after the current line being evaluated, for example, positive slope peaks (e.g., locations having positive slope values above the predefined positive slope threshold) within a predefined y-dimension offset of the identified positive slope peak location (x) may be identified and/or their respective locations recorded. Proximate slope peak identification and/or locating may be performed and/or repeated for all positive slope peaks identified within the current line being evaluated. In some embodiments, each positive slope peak having proximate positive slope peaks may be recorded as a positive slope peak point group.

According to some embodiments, the method 600 may comprise calculating a mathematical fit correlation for each positive slope peak point group, at 608. For each group of positive slope peak points identified at 604, for example, a least squares linear fit may be utilized to calculate a fit correlation. In some embodiments, such as in the case that the fit correlation exceeds a predefined fit correlation threshold, the positive slope peak point group may be identified and/or classified, at 610, as a first tape/course edge or "left tape edge" (or "left course edge"). According to some embodiments, the x-coordinate of the left tape edge may be recorded in association with the current line being evaluated. In some embodiments, the calculating of the mathematical fit correlation may be conducted and/or repeated for all positive slope peak groups for the current line being evaluated.

According to some embodiments, the method 600 may comprise a determination if the current positive slope peak point is within a defined lateral band of corresponding positive slope peak points in adjacent lines (e.g., a basic mathematical correlation), at 608. For each group of positive slope peak points identified at 604, for example, a lateral width band may be utilized to determine if the current positive slope peak point falls close enough to them to be considered fitting to a common edge line. In some embodiments, such as in the case that the positive slope peak point is within a defined lateral band of corresponding positive slope peak points in adjacent lines, the positive slope peak point group may be identified and/or classified, at 610, as a first tape/course edge or "left tape edge" (or "left course edge"). According to some embodiments, the x-coordinate of the left tape edge may be recorded in association with the current line being evaluated. In some embodiments, the calculating of the lateral band proximity correlation may be conducted and/or repeated for all positive slope peak groups for the current line being evaluated.

According to some embodiments, the method 600 may comprise determining negative slope locations, at 612. For each scan line (i.e., along the x-axis) represented by the subset of available point data, for example, negative slope locations (dz/dx) may be identified. In some embodiments, slope locations having slope values below a predefined negative slope threshold may be recorded as negative slope peak locations (x).

In some embodiments, the method 600 may comprise locating proximate negative slope peak locations, at 614. Over a group of lines before and after the current line being evaluated, for example, negative slope peaks (e.g., locations having negative slope values below the predefined negative slope threshold; or above the threshold, in the case that absolute values are utilized) within a predefined y-dimension offset of the identified negative slope peak location (x) may be identified and/or their respective locations recorded. Proximate slope peak identification and/or locating may be performed and/or repeated for all negative slope peaks identified within the current line being evaluated. In some embodiments, each negative slope peak having proximate negative slope peaks may be recorded as a negative slope peak point group.

According to some embodiments, the method 600 may comprise calculating a mathematical fit correlation for each negative slope peak point group, at 616. For each group of negative slope peak points identified at 610, for example, a least squares linear fit may be utilized to calculate a fit correlation. In some embodiments, such as in the case that the fit correlation exceeds a predefined fit correlation threshold, the negative slope peak point group may be identified and/or classified, at 618, as a second tape/course edge or "right tape edge" (or "right course edge"). According to some embodiments, the x-coordinate of the right tape edge may be recorded in association with the current line being evaluated. In some embodiments, the calculating of the mathematical fit correlation may be conducted and/or repeated for all negative slope peak groups for the current line being evaluated.

According to some embodiments, the method 600 may comprise a determination if the current negative slope peak point is within a defined lateral band of corresponding negative slope peak points in adjacent lines (e.g., a basic mathematical correlation), at 608. For each group of negative slope peak points identified at 604, for example, a lateral width band may be utilized to determine if the current negative slope peak point falls close enough to them to be considered fitting to a common edge line. In some embodiments, such as in the case that the negative slope peak point is within a defined lateral band of corresponding negative slope peak points in adjacent lines, the negative slope peak point group may be identified and/or classified, at 610, as a first tape/course edge or "right tape edge" (or "right course edge"). According to some embodiments, the x-coordinate of the right tape edge may be recorded in association with the current line being evaluated. In some embodiments, the calculating of the lateral band proximity correlation may be conducted and/or repeated for all negative slope peak groups for the current line being evaluated.

Figure 7:
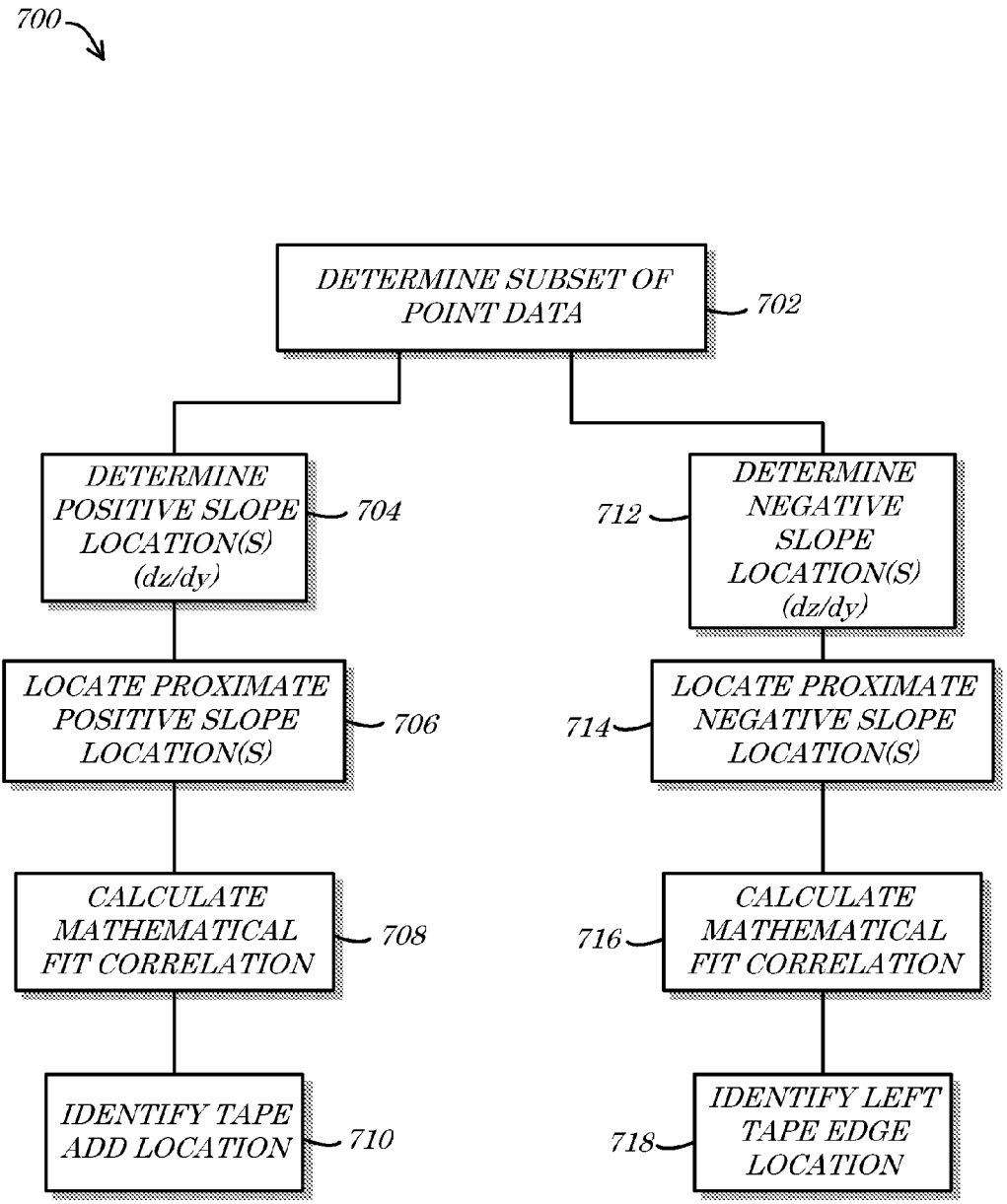
FIG. 7 is a flow diagram of a method according to some embodiments.

Turning now to FIG. 7, a flow diagram of a method 700 according to some embodiments is shown. In some embodiments, the method 700 may comprise a portion of the method 500 such as one or more of the detecting of the layup surface features at 506, the storing of the layup feature data at 508, the evaluating of the identified features at 510, and/or portions or combinations thereof. The method 700 may comprise, for example, a method of detecting, identifying, and/or locating composite layup tape and/or course ends (e.g., beginning or "add" points and end or "drop" points).

In some embodiments, the method 700 may comprise determining a subset of available point data, at 702. The available point data may comprise, for example, the point data processed at 504 by the method 500. Interpolated, smoothed, and/or re-oriented point data descriptive of a layup surface may be received and/or acquired as input into a specially-programmed procedure and/or module for identifying tape and/or course ends, for example. According to some embodiments, the processed point data may comprise data that has been smoothed in the x-direction (i.e., in the direction along a particular scan line). In some embodiments, a predetermined number and/or percentage of scan lines and/or points may be skipped over, with the remaining scan line and/or point data defining the determined, selected, and/or identified subset of point data to be utilized for layup feature detection. The number of scan lines and/or points to skip may be predetermined based on a layup parameter determined at the determining of the point data at 502, for example, and/or may be derived based on parameters descriptive of the layup sequence and/or associated scanning process. In some embodiments, a number of scan lines and/or points may be skipped at either or both of the beginning of the point data (e.g., data descriptive of initial surface scanning) and the end of the point data (e.g., data descriptive of final surface scanning). According to some embodiments, the point data may be truncated to define the subset of available point data to be utilized for feature location. In some embodiments, the subset of available point data selected for analysis may be the same subset determined or identified at 602 of the method 600. In some embodiments, the subset determined at 602 may comprise a first subset of data and the subset determined at 702 may comprise a second subset of data. In some embodiments, the first and second subsets may be different (i.e., a different subset may be utilized to analyze and/or identify/locate tape/course ends in the method 700 than is utilized to analyze, locate, and/or identify tape/course edges in the method 600).

According to some embodiments, the method 700 may comprise determining positive slope locations, at 704. For each x-coordinate or scan axis line (i.e., along the y-axis) represented by the subset of available point data, for example, positive slope locations (dz/dy) may be identified. In some embodiments, slope locations having slope values above a predefined positive slope threshold may be recorded as positive slope peak locations (y).

In some embodiments, the method 700 may comprise locating proximate positive slope peak locations, at 706. Over a group of scan axis lines before and after the current axis line being evaluated, for example, positive slope peaks (e.g., locations having positive slope values above the predefined positive slope threshold) within a predefined x-dimension offset of the identified positive slope peak location (y) may be identified and/or their respective locations recorded. Proximate slope peak identification and/or locating may be performed and/or repeated for all positive slope peaks identified within the current scan axis line being evaluated. In some embodiments, each positive slope peak having proximate positive slope peaks may be recorded as a positive slope peak point group.

According to some embodiments, the method 700 may comprise calculating a mathematical fit correlation for each positive slope peak point group, at 708. For each group of positive slope peak points identified at 704, for example, a least squares linear fit may be utilized to calculate a fit correlation. In some embodiments, such as in the case that the fit correlation exceeds a predefined fit correlation threshold, the positive slope peak point group may be identified and/or classified, at 710, as a first tape/course end or "tape add point". According to some embodiments, the y-coordinate of the tape add point may be recorded in association with the current scan axis line being evaluated. In some embodiments, the calculating of the mathematical fit correlation may be conducted and/or repeated for all positive slope peak groups for the current scan axis line being evaluated.

According to some embodiments, the method 700 may comprise a determination if the current positive slope peak point is within a defined lateral band of corresponding positive slope peak points in adjacent points along a scan (e.g., a basic mathematical correlation), at 708. For each group of positive slope peak points identified at 704, for example, a lateral width band may be utilized to determine if the current positive slope peak point falls close enough to be considered fitting to a common Add line. In some embodiments, such as in the case that the positive slope peak point is within a defined lateral band of corresponding positive slope peak points in adjacent lines, the positive slope peak point group may be identified and/or classified, at 610, as a first tape/course end or "tape add location" (or "course add location"). According to some embodiments, the y-coordinate of the add location may be recorded in association with the current line being evaluated. In some embodiments, the calculating of the lateral band proximity correlation may be conducted and/or repeated for all positive slope peak groups for the current scan line being evaluated.

According to some embodiments, the method 700 may comprise a determination if the current add line indicators should be labelled as points on an add line. The points may be identified, for example, as belonging to an add line in a case where they constitute a minimum percentage of points expected for one tape width based on the nominal x-axis point-to-point line spacing.

According to some embodiments, the method 700 may comprise determining negative slope locations, at 712. For each scan axis line (i.e., along the y-axis) represented by the subset of available point data, for example, negative slope locations (dz/dy) may be identified. In some embodiments, slope locations having slope values below a predefined negative slope threshold may be recorded as negative slope peak locations (y).

In some embodiments, the method 700 may comprise locating proximate negative slope peak locations, at 714. Over a group of scan axis lines before and after the current scan axis line being evaluated, for example, negative slope peaks (e.g., locations having negative slope values below the predefined negative slope threshold; or above the threshold, in the case that absolute values are utilized) within a predefined x-dimension offset of the identified negative slope peak location (y) may be identified and/or their respective locations recorded. Proximate slope peak identification and/or locating may be performed and/or repeated for all negative slope peaks identified with respect to the current scan axis line being evaluated. In some embodiments, each negative slope peak having proximate negative slope peaks may be recorded as a negative slope peak point group.

According to some embodiments, the method 700 may comprise calculating a mathematical fit correlation for each negative slope peak point group, at 716. For each group of negative slope peak points identified at 710, for example, a least squares linear fit may be utilized to calculate a fit correlation. In some embodiments, such as in the case that the fit correlation exceeds a predefined fit correlation threshold, the negative slope peak point group may be identified and/or classified, at 718, as a second tape/course end or "tape drop point" (or "course drop point"). According to some embodiments, the y-coordinate of the tape drop point may be recorded in association with the current scan axis line being evaluated. In some embodiments, the calculating of the mathematical fit correlation may be conducted and/or repeated for all negative slope peak groups for the current scan axis line being evaluated.

According to some embodiments, the method 700 may comprise a determination if the current negative slope peak point is within a defined lateral band of corresponding negative slope peak points in adjacent points along a scan (e.g., a basic mathematical correlation), at 708. For each group of negative slope peak points identified at 704, for example, a lateral width band may be utilized to determine if the current negative slope peak point falls close enough to be considered fitting to a common drop line. In some embodiments, such as in the case that the negative slope peak point is within a defined lateral band of corresponding positive slope peak points in adjacent lines, the negative slope peak point group may be identified and/or classified, at 610, as a second tape/course end "tape drop location" (or "course drop location"). According to some embodiments, the y-coordinate of the drop location may be recorded in association with the current line being evaluated. In some embodiments, the calculating of the lateral band proximity correlation may be conducted and/or repeated for all negative slope peak groups for the current scan line being evaluated.

According to some embodiments, the method 700 may comprise a determination if the current drop line indicators should be labelled as points on a drop line. The points may be identified, for example, as belonging to a drop line in a case where they constitute a minimum percentage of points expected for one tape width based on the nominal x point-to-point line spacing.

Figure 8:
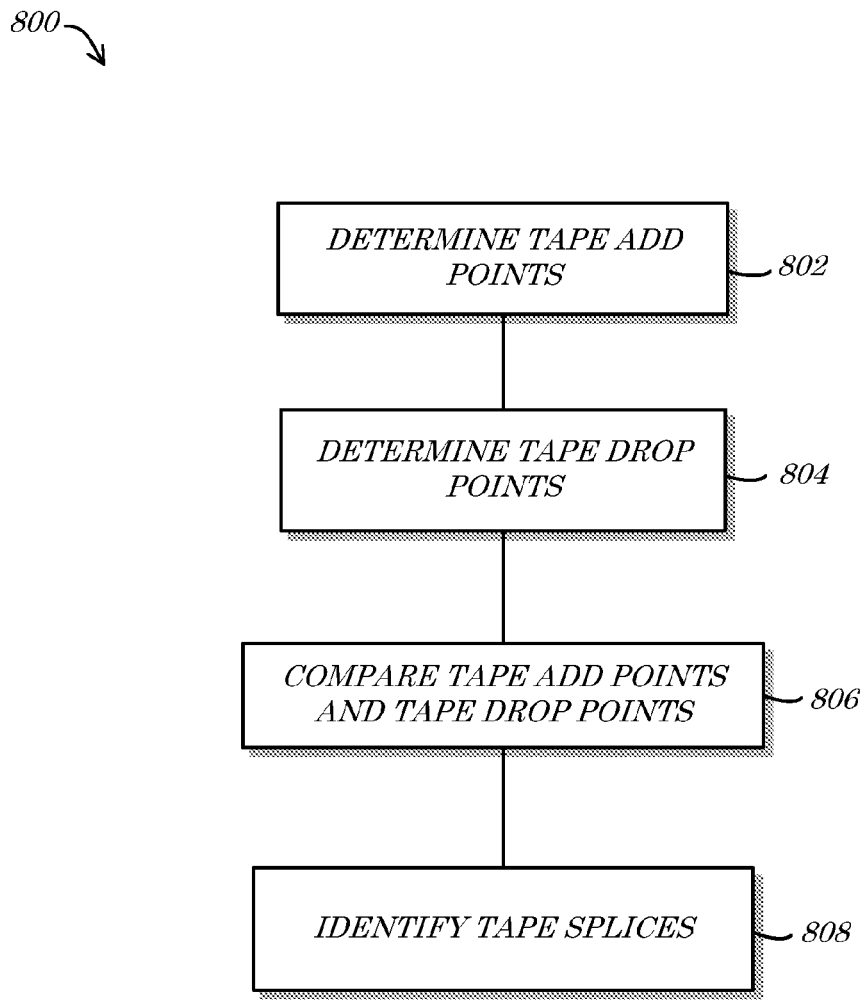
FIG. 8 is a flow diagram of a method according to some embodiments.

Referring now to FIG. 8, a flow diagram of a method 800 according to some embodiments is shown. In some embodiments, the method 800 may comprise a portion of the method 500 such as one or more of the detecting of the layup surface features at 506, the storing of the layup feature data at 508, the evaluating of the identified features at 510, and/or portions or combinations thereof. The method 800 may comprise, for example, a method of detecting, identifying, and/or locating composite tape splices.

In some embodiments, the method 800 may comprise a portion or extension of the method 700 of FIG. 7. Once tape add points and tape drop points have been identified for single tape, for example, the method 800 may be utilized to identify tape splices utilizing the tape add point and tape drop point data. The method 800 may comprise, for example, determining tape add points, at 802. Tape add point locations determined at 706 of the method 700 of FIG. 7, for example, may be read from memory (e.g., from a database or hard drive in the case that the method 800 is executed at some hours or days subsequent to an execution of the method 700, or from RAM or cache in the case that the method 800 is executed at some seconds or minutes subsequent to an execution of the method 700). In some embodiments, the tape add point data accessed and/or loaded as input (e.g., into RAM) may comprise all tape add points identified for a particular scan axis line (e.g., along the y-axis).

According to some embodiments, the method 800 may comprise determining tape drop points, at 804. Tape drop point locations determined at 712 of the method 700 of FIG. 7, for example, may be read from memory (e.g., from a database or hard drive in the case that the method 800 is executed at some hours or days subsequent to an execution of the method 700, or from RAM or cache in the case that the method 800 is executed at some seconds or minutes subsequent to an execution of the method 700). In some embodiments, the tape drop point data accessed and/or loaded as input (e.g., into RAM) may comprise all tape drop points identified for the particular scan axis line (e.g., along the y-axis) for which the tape add points are determined or identified at 802.

In some embodiments, the method 800 may comprise comparing the tape add points and tape drop points, at 806. The y-coordinate of a tape add point may be subtracted from the y-coordinate of a consecutively-occurring tape drop point, for example, to derive or calculate a distance between the add/drop pair of points. In such a manner, for example, a length of each particular tape splice segment may be determined.

According to some embodiments, the method 800 may comprise identifying tape splices, at 808. A tape splice may be defined, for example, as a tape segment having a length less than (or less than or equal to) a predefined splice length threshold. Accordingly, in some embodiments, the distance between consecutive tape add point and tape drop points determined based on the comparing at 804 may be compared to such a splice length threshold to determine if the calculated length for any particular segment is less than (or less than or equal to) the applicable splice length threshold (e.g., one and one half inches (1.5")). In the case that a particular segment length is determined to meet the splice length criteria, the respective tape add point and tape drop point may be flagged and/or identified as a "splice add point" and a "splice drop point", respectively. In some embodiments, such as in the case that manufacturing criteria requires fewer than a threshold number and/or amount (e.g., length or area) of splices per unit of layup area, the number, area, total length, percentage, and/or other metric defining a quantity of identified splices may be utilized to determine if the analyzed layup area falls within or outside of the criteria. In the case that the layup area contains more splices than are allowed, a warning or error message may be provided.

IV. Apparatus and Articles of Manufacture

Figure 9:
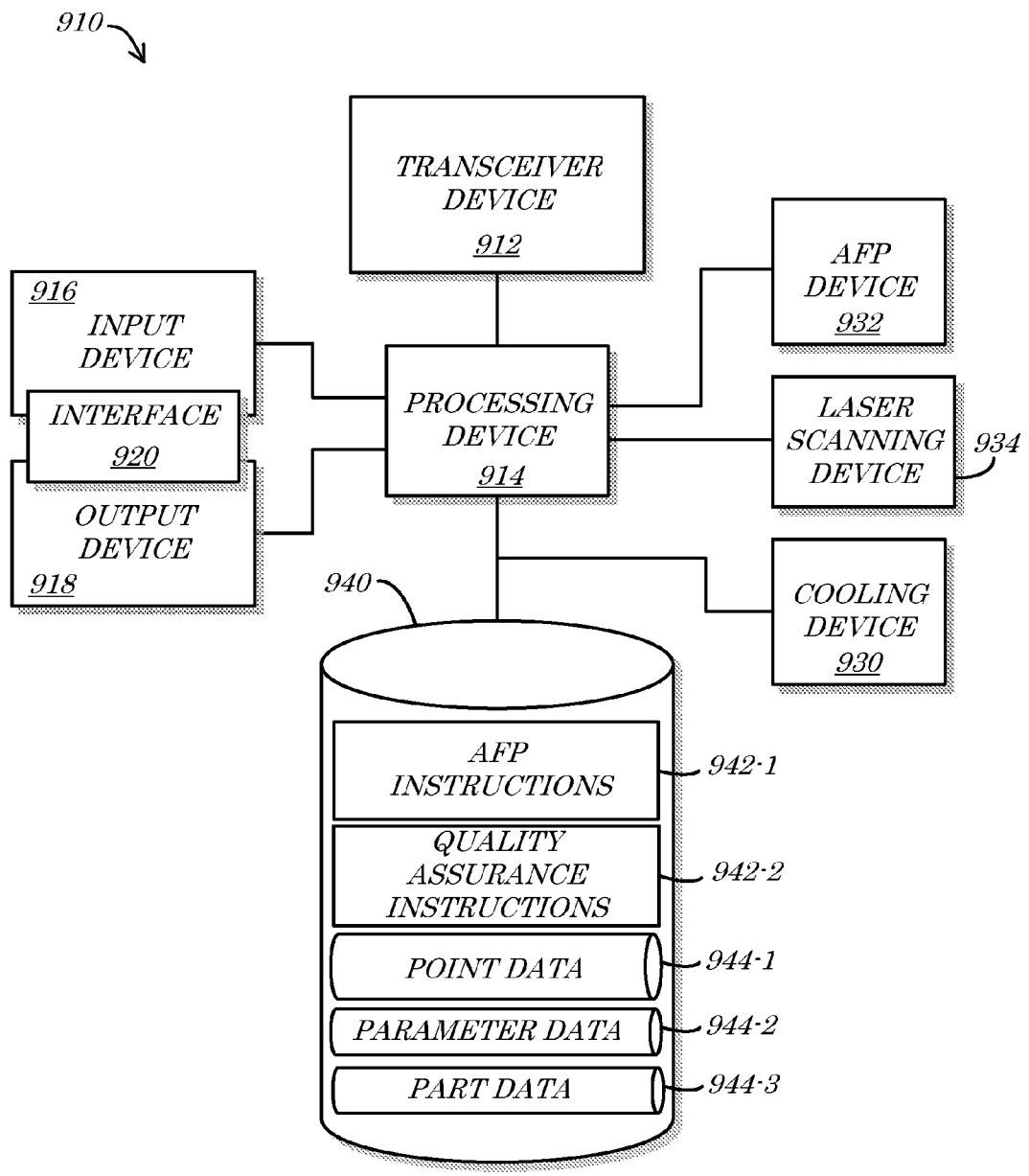
FIG. 9 is a block diagram of an example system according to some embodiments.
Figure 10A:
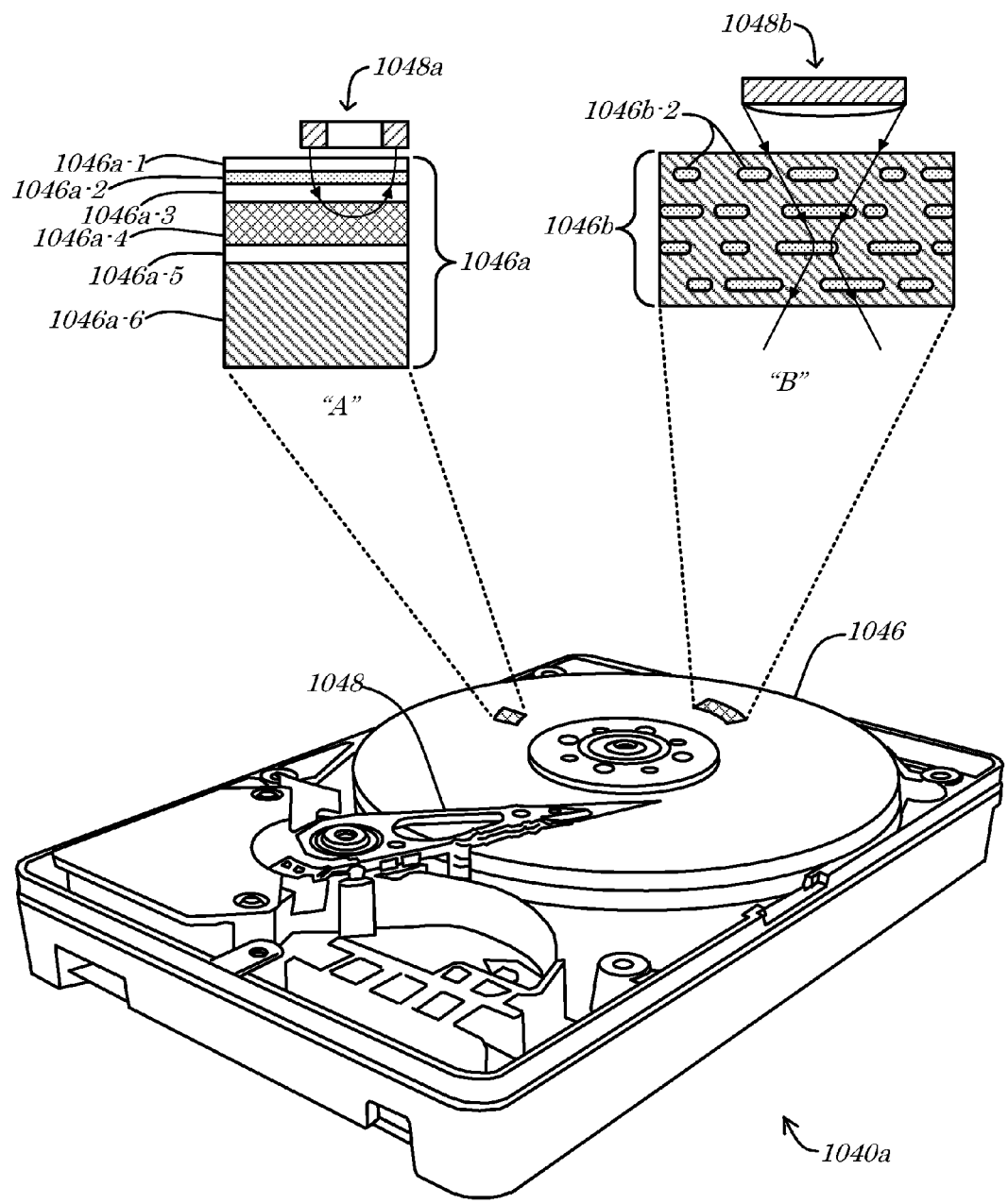
FIG. 10A, FIG. 10B, FIG. 10C, FIG. 10D, and FIG. 10E are perspective diagrams of exemplary data storage devices according to some embodiments.
Figure 10B:
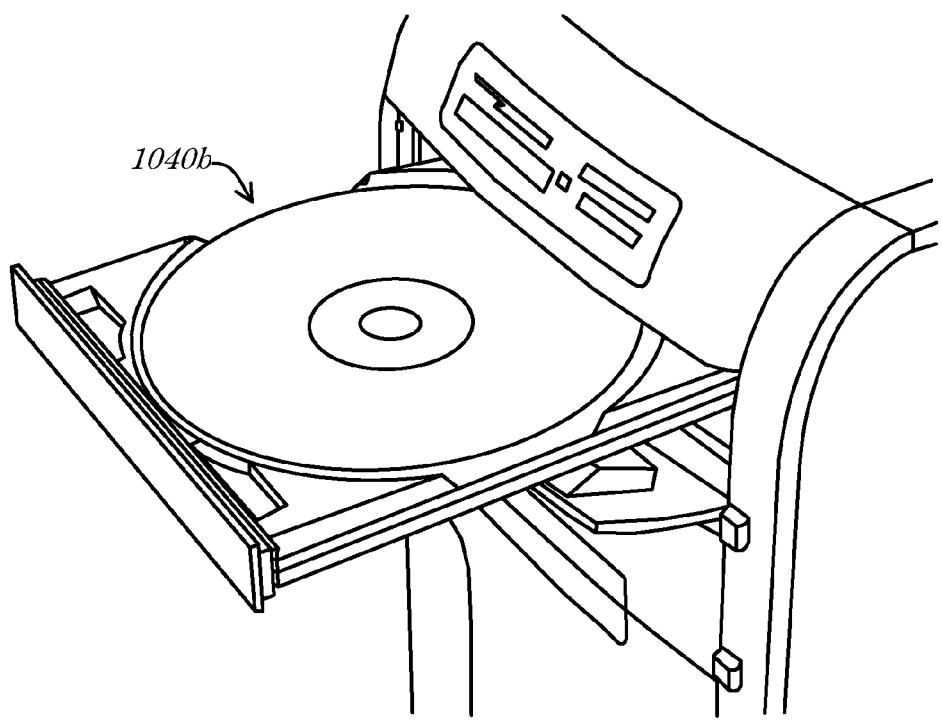
Figure 10C:
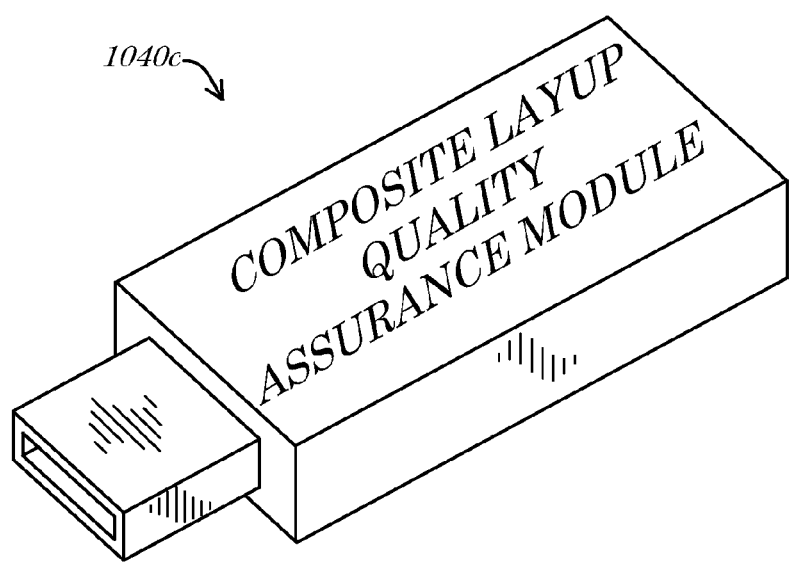
Figure 10D:
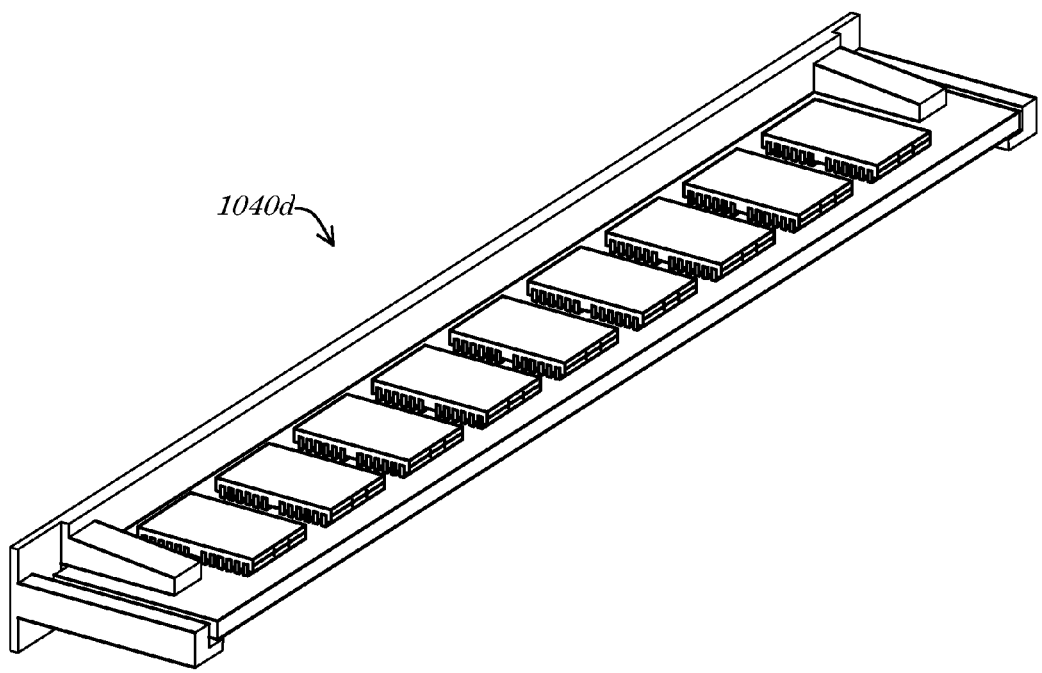
Figure 10E:
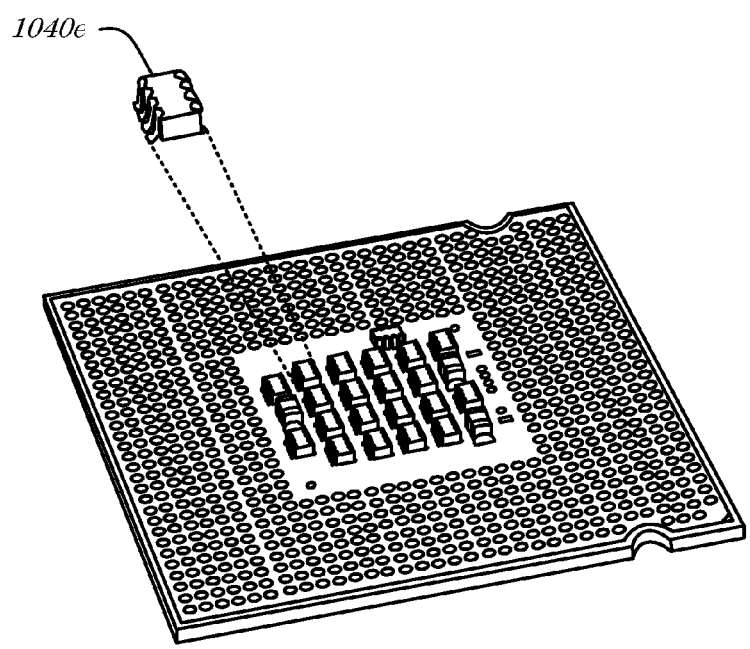

Turning to FIG. 9, a block diagram of an apparatus (or system) 910 according to some embodiments is shown. In some embodiments, the apparatus 910 may be similar in configuration and/or functionality to the controller device 110 of FIG. 1 herein, and/or may otherwise comprise a portion or variation of the system 100 of FIG. 1 herein. The apparatus 910 may, for example, execute, process, facilitate, and/or otherwise be associated with the methods 500, 600, 700, 800 described in conjunction with FIG. 5, FIG. 6, FIG. 7, and/or FIG. 8 herein, and/or one or more portions or combinations thereof. In some embodiments, the apparatus 910 may comprise a transceiver device 912, one or more processing devices 914, an input device 916, an output device 918, an interface 920, a cooling device 930, and AFP device 932, a laser scanning device 934, and/or a memory device 940 (storing various programs and/or instructions 942 and data 944). According to some embodiments, any or all of the components 912, 914, 916, 918, 920, 930, 932, 934, 940, 942, 944 of the apparatus 910 may be similar in configuration and/or functionality to any similarly named and/or numbered components described herein. Fewer or more components 912, 914, 916, 918, 920, 930, 932, 934, 940, 942, 944 and/or various configurations of the components 912, 914, 916, 918, 920, 930, 932, 934, 940, 942, 944 may be included in the apparatus 910 without deviating from the scope of embodiments described herein.

In some embodiments, the transceiver device 912 may comprise any type or configuration of bi-directional electronic communication device that is or becomes known or practicable. The transceiver device 912 may, for example, comprise a Network Interface Card (NIC), a telephonic device, a cellular network device, a router, a hub, a modem, and/or a communications port or cable. In some embodiments, the transceiver device 912 may be coupled to provide data to a user device (not shown in FIG. 9), such as in the case that the apparatus 910 is utilized to provide a data processing interface to a user and/or to provide composite layup quality assurance data processing results, as described herein. The transceiver device 912 may, for example, comprise a wireless network transmission device that sends signals indicative of quality assurance data processing interface components and/or data processing result-based commands to a user handheld, mobile, and/or telephone device. According to some embodiments, the transceiver device 912 may also or alternatively be coupled to the processing device 914. In some embodiments, the transceiver device 912 may comprise an IR, RF, Bluetooth™, and/or Wi-Fi® network device coupled to facilitate communications between the processing device 914 and another device (such as a user device and/or a third-party device; not shown in FIG. 9).

According to some embodiments, the processing device 914 may be or include any type, quantity, and/or configuration of electronic and/or computerized processor that is or becomes known. The processing device 914 may comprise, for example, an Intel® IXP 2800 network processor or an Intel® XEON™ Processor coupled with an Intel® E7501 chipset. In some embodiments, the processing device 914 may comprise multiple inter-connected processors, microprocessors, and/or micro-engines. According to some embodiments, the processing device 914 (and/or the apparatus 910 and/or portions thereof) may be supplied power via a power supply (not shown) such as a battery, an Alternating Current (AC) source, a Direct Current (DC) source, an AC/DC adapter, solar cells, and/or an inertial generator. In the case that the apparatus 910 comprises a server such as a blade server, necessary power may be supplied via a standard AC outlet, power strip, surge protector, a PDU, and/or Uninterruptible Power Supply (UPS) device (none of which are shown in FIG. 9).

In some embodiments, the input device 916 and/or the output device 918 are communicatively coupled to the processing device 914 (e.g., via wired and/or wireless connections and/or pathways) and they may generally comprise any types or configurations of input and output components and/or devices that are or become known, respectively. The input device 916 may comprise, for example, a keyboard that allows an operator of the apparatus 910 to interface with the apparatus 910 (e.g., by a user, such as a quality assurance inspector). The output device 918 may, according to some embodiments, comprise a display screen and/or other practicable output component and/or device, such as an actuator and/or robotic servo and/or motor assembly coupled to reposition one or more manufacturing and/or quality assurance devices as described herein. The output device 918 may, for example, provide a quality assurance data processing interface such as the interface 920 to a user (e.g., via a website and/or via laser line projection on a composite layup surface and/or mold thereof). In some embodiments, the interface 920 may comprise portions and/or components of either or both of the input device 916 and the output device 918. According to some embodiments, the input device 916 and/or the output device 918 may, for example, comprise and/or be embodied in an input/output and/or single device such as a touch-screen monitor (e.g., that enables both input and output via the interface 920).

In some embodiments, the apparatus 910 may comprise the cooling device 930. According to some embodiments, the cooling device 930 may be coupled (physically, thermally, and/or electrically) to the processing device 914 and/or to the memory device 940. The cooling device 930 may, for example, comprise a fan, heat sink, heat pipe, radiator, cold plate, and/or other cooling component or device or combinations thereof, configured to remove heat from portions or components of the apparatus 910. In some embodiments, the cooling device 930 may comprise a thermocouple and/or refrigerant device coupled to the AFP device 932 and/or a prepreg material storage unit thereof (not separately shown), such as to cool and/or maintain a desired working temperature of one or more spools of prepreg tapes to be laid up on a mold or tool.

According to some embodiments, the apparatus 910 may comprise a system that includes the AFP device 932 and/or the laser scanning device 934. The processing device 914 may be operatively coupled to and/or in communication with either or both of the AFP device 932 and the laser scanning device 934, for example, such as to receive point data from the laser scanning device 934 and/or to transmit commands (e.g., positioning and/or other function commands) to the AFP device 932. In some embodiments, the apparatus/system 910 may not include the AFP device 932 and the laser scanning device 934, but may be in communication therewith, such as via the transceiver device 912, the input device 916, and/or the output device 918.

The memory device 940 may comprise any appropriate information storage device that is or becomes known or available, including, but not limited to, units and/or combinations of magnetic storage devices (e.g., a hard disk drive), optical storage devices, and/or semiconductor memory devices such as RAM devices, Read Only Memory (ROM) devices, Single Data Rate Random Access Memory (SDR-RAM), Double Data Rate Random Access Memory (DDR-RAM), and/or Programmable Read Only Memory (PROM). The memory device 940 may, according to some embodiments, store one or more of AFP instructions 942-1 (e.g., CNC programming), quality assurance instructions 942-2, point data 944-1 (e.g., composite layup surface point cloud data), parameter data 944-2 (e.g., composite layup parameter data such as tape width, gap thresholds, etc.), and/or part data 944-3 (e.g., feature and/or flaw files). In some embodiments, the AFP instructions 942-1, quality assurance instructions 942-2, point data 944-1, parameter data 944-2, and/or part data 944-3 may be utilized by the processing device 914 to provide output information via the output device 918 and/or the transceiver device 912.

According to some embodiments, the AFP instructions 942-1 may be operable to cause the processing device 914 to process the point data 944-1, parameter data 944-2, and/or part data 944-3. Point data 944-1, parameter data 944-2, and/or part data 944-3 received via the input device 916 and/or the transceiver device 912 may, for example, be analyzed, sorted, filtered, decoded, decompressed, ranked, scored, plotted, and/or otherwise processed by the processing device 914 in accordance with the AFP instructions 942-1. In some embodiments, point data 944-1, parameter data 944-2, and/or part data 944-3 may be fed by the processing device 914 through one or more mathematical and/or statistical formulas and/or models in accordance with the AFP instructions 942-1 to cause the AFP device 932 to deposit composite layup on a mold and/or to cause the laser scanning device 934 to acquired data descriptive of a composite layup surface, as described herein.

In some embodiments, the quality assurance instructions 942-2 may be operable to cause the processing device 914 to process the point data 944-1, parameter data 944-2, and/or part data 944-3. Point data 944-1, parameter data 944-2, and/or part data 944-3 received via the input device 916 and/or the transceiver device 912 may, for example, be analyzed, sorted, filtered, decoded, decompressed, ranked, scored, plotted, and/or otherwise processed by the processing device 914 in accordance with the quality assurance instructions 942-2. In some embodiments, point data 944-1, parameter data 944-2, and/or part data 944-3 may be fed by the processing device 914 through one or more mathematical and/or statistical formulas and/or models in accordance with the quality assurance instructions 942-2 perform automated composite layup surface quality assurance (and/or automated repairs/reworks and/or facilitation thereof), as described herein.

Any or all of the exemplary instructions 942 and data types 944 described herein and other practicable types of data may be stored in any number, type, and/or configuration of memory devices that is or becomes known. The memory device 940 may, for example, comprise one or more data tables or files, databases, table spaces, registers, and/or other storage structures. In some embodiments, multiple databases and/or storage structures (and/or multiple memory devices 940) may be utilized to store information associated with the apparatus 910. According to some embodiments, the memory device 940 may be incorporated into and/or otherwise coupled to the apparatus 910 (e.g., as shown) or may simply be accessible to the apparatus 910 (e.g., externally located and/or situated).

Referring to FIG. 10A, FIG. 10B, FIG. 10C, FIG. 10D, and FIG. 10E, perspective diagrams of exemplary data storage devices 1040a-e according to some embodiments are shown. The data storage devices 1040a-e may, for example, be utilized to store instructions and/or data such as the AFP instructions 942-1, quality assurance instructions 942-2, point data 944-1, parameter data 944-2, and/or part data 944-3, each of which is described in reference to FIG. 9 herein. In some embodiments, instructions stored on the data storage devices 1040a-e may, when executed by one or more threads, cores, and/or processors (such as the processor device 914 of FIG. 9), cause the implementation of and/or facilitate the methods 500, 600, 700, 800 described in conjunction with FIG. 5, FIG. 6, FIG. 7, and/or FIG. 8 herein, and/or portions or combinations thereof.

According to some embodiments, a first data storage device 1040a may comprise one or more various types of internal and/or external hard drives. The first data storage device 1040a may, for example, comprise a data storage medium 1046 that is read, interrogated, and/or otherwise communicatively coupled to and/or via a disk reading device 1048. In some embodiments, the first data storage device 1040a and/or the data storage medium 1046 may be configured to store information utilizing one or more magnetic, inductive, and/or optical means (e.g., magnetic, inductive, and/or optical-encoding). The data storage medium 1046, depicted as a first data storage medium 1046a for example (e.g., breakout cross-section "A"), may comprise one or more of a polymer layer 1046a-1, a magnetic data storage layer 1046a-2, a non-magnetic layer 1046a-3, a magnetic base layer 1046a-4, a contact layer 1046a-5, and/or a substrate layer 1046a-6. According to some embodiments, a magnetic read head 1046a may be coupled and/or disposed to read data from the magnetic data storage layer 1046a-2.

In some embodiments, the data storage medium 1046, depicted as a second data storage medium 1046b for example (e.g., breakout cross-section "B"), may comprise a plurality of data points 1046b-2 disposed with the second data storage medium 1046b. The data points 1046b-2 may, in some embodiments, be read and/or otherwise interfaced with via a laser-enabled read head 1048b disposed and/or coupled to direct a laser beam through the second data storage medium 1046b.

In some embodiments, a second data storage device 1040b may comprise a CD, CD-ROM, DVD, Blu-Ray™ Disc, and/or other type of optically-encoded disk and/or other storage medium that is or becomes know or practicable. In some embodiments, a third data storage device 1040c may comprise a USB keyfob, dongle, and/or other type of flash memory data storage device that is or becomes know or practicable. In some embodiments, a fourth data storage device 1040d may comprise RAM of any type, quantity, and/or configuration that is or becomes practicable and/or desirable. In some embodiments, the fourth data storage device 1040d may comprise an off-chip cache such as a Level 2 (L2) cache memory device. According to some embodiments, a fifth data storage device 1040e may comprise an on-chip memory device such as a Level 1 (L1) cache memory device.

The data storage devices 1040a-e may generally store program instructions, code, and/or modules that, when executed by a processing device cause a particular machine to function in accordance with one or more embodiments described herein. The data storage devices 1040a-e depicted in FIG. 10A, FIG. 10B, FIG. 10C, FIG. 10D, and FIG. 10E are representative of a class and/or subset of computer-readable media that are defined herein as "computer-readable memory" (e.g., non-transitory memory devices as opposed to transmission devices or media).

The terms "computer-readable medium" and "computer-readable memory" refer to any medium that participates in providing data (e.g., instructions) that may be read by a computer and/or a processor. Such a medium may take many forms, including but not limited to non-volatile media, volatile media, and other specific types of transmission media. Non-volatile media include, for example, optical or magnetic disks and other persistent memory. Volatile media include DRAM, which typically constitutes the main memory. Other types of transmission media include coaxial cables, copper wire, and fiber optics, including the wires that comprise a system bus coupled to the processor.

Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable medium" and/or "tangible media" specifically exclude signals, waves, and wave forms or other intangible or transitory media that may nevertheless be readable by a computer.

Various forms of computer-readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined above and includes many exemplary protocols that are also applicable here.

V. Terms and Rules of Interpretation

Throughout the description herein and unless otherwise specified, the following terms may include and/or encompass the example meanings provided in this section. These terms and illustrative example meanings are provided to clarify the language selected to describe embodiments both in the specification and in the appended claims, and accordingly, are not intended to be limiting. While not generally limiting and while not limiting for all described embodiments, in some embodiments, the terms are specifically limited to the example definitions and/or examples provided. Other terms are defined throughout the present description.

Some embodiments described herein are associated with a "module". As utilized herein, the term "module" may generally be descriptive of any combination of hardware, electronic circuitry and/or other electronics (such as logic chips, logical gates, and/or other electronic circuit elements or components), hardware (e.g., physical devices such as hard disks, solid-state memory devices, and/or computer components such as processing units or devices), firmware, and/or software or microcode.

Some embodiments described herein are associated with a "user device", a "remote device", or a "network device". As used herein, each of a "user device" and a "remote device" is a subset of a "network device". The "network device", for example, may generally refer to any device that can communicate via a network, while the "user device" may comprise a network device that is owned and/or operated by or otherwise associated with a particular user (and/or group of users—e.g., via shared login credentials and/or usage rights), and while a "remote device" may generally comprise a device remote from a primary device or system component and/or may comprise a wireless and/or portable network device. Examples of user, remote, and/or network devices may include, but are not limited to: a PC, a computer workstation, a computer server, a printer, a scanner, a facsimile machine, a copier, a Personal Digital Assistant (PDA), a storage device (e.g., a disk drive), a hub, a router, a switch, and a modem, a video game console, or a wireless or cellular telephone. User, remote, and/or network devices may, in some embodiments, comprise one or more network components.

As used herein, the term "network component" may refer to a user, remote, or network device, or a component, piece, portion, or combination of user, remote, or network devices. Examples of network components may include a Static Random Access Memory (SRAM) device or module, a network processor, and a network communication path, connection, port, or cable.

In addition, some embodiments are associated with a "network" or a "communication network." As used herein, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. Networks may be or include a plurality of interconnected network devices. In some embodiments, networks may be hard-wired, wireless, virtual, neural, and/or any other configuration or type that is or becomes known. Communication networks may include, for example, devices that communicate directly or indirectly, via a wired or wireless medium such as the Internet, intranet, a Local Area Network (LAN), a Wide Area Network (WAN), a cellular telephone network, a Bluetooth® network, a Near-Field Communication (NFC) network, a Radio Frequency (RF) network, a Virtual Private Network (VPN), Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), and/or system to system (S2S).

As used herein, the terms "information" and "data" may be used interchangeably and may refer to any data, text, voice, video, image, message, bit, packet, pulse, tone, waveform, and/or other type or configuration of signal and/or information. Information may comprise information packets transmitted, for example, in accordance with the Internet Protocol Version 6 (IPv6) standard. Information may, according to some embodiments, be compressed, encoded, encrypted, and/or otherwise packaged or manipulated in accordance with any method that is or becomes known or practicable.

The term "indication", as used herein (unless specified otherwise), may generally refer to any indicia and/or other information indicative of or associated with a subject, item, entity, and/or other object and/or idea. As used herein, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

In some embodiments, a method of automated composite layup inspection may comprise: (i) receiving, by a processing device, information describing a three-dimensional point cloud of a top surface of a composite layup, the top surface comprising a region of one or more courses of composite layup material, each course comprising a plurality of composite material tapes; (ii) determining, by the processing device and based on the three-dimensional point cloud, and at least one algorithm, a presence and location of one or more flaws on the top surface; and/or (iii) evaluating, by the processing device and based on the one or more flaws on the top surface, whether the composite layup should be at least one of: (1) accepted as is; (2) repaired to resolve the one or more flaws; and (3) rejected. According to some embodiments, the three-dimensional point cloud may comprise data descriptive of a series of points collected from a series of roughly parallel lines, wherein the series of roughly parallel lines spans across the top surface, and describes the three-dimensional characteristics of the top surface. In some embodiments, the series of roughly parallel lines may comprise a multitude of data points. According to some embodiments, a spacing between the multitude of data points may be less than the width of one tape of the composite layup material. In some embodiments, a spacing between the roughly parallel lines may be less than the location tolerance for an Add or Drop feature. In some embodiments the height or thickness resolution may be less that the thickness of one tape of the composite layup material.

According to some embodiments, a spacing between the multitude of data points within the X/Y scan plane may be less than one hundred and twenty-five (125) microns. In some embodiments, a spacing between the multitude of data points may be between one (1) and seventy-five (75) microns. According to some embodiments, a spacing between the multitude of data points may between five (5) and twenty-five (25) microns. In some embodiments, the three-dimensional point cloud may comprise data descriptive of a multitude of data points spanning across the top surface and describing the three-dimensional characteristics of the top surface. In some embodiments, the multitude of data points may comprise a grid of data points. According to some embodiments, the multitude of data points may comprise a number of data points equal to or greater than fifty thousand (50,000) data points per square inch of the top surface. In some embodiments, the multitude of data points may comprise between one thousand (1,000) and fifty thousand (50,000) data points per square inch of the top surface. According to some embodiments, the multitude of data points may comprise between thirty thousand (30,000) and forty thousand (40,000) data points per square inch of the top surface.

In some embodiments, the presence and location of one or more flaws on the top surface may be determined using the at least one algorithm with the three-dimensional point cloud, wherein the at least one algorithm is used to evaluate a first portion of the three-dimensional point cloud to determine the presence and location of one or more first flaws on the top surface, and the at least one algorithm may then be used to evaluate a second portion of the three-dimensional point cloud to determine the presence and location of one or more second flaws on the top surface. According to some embodiments, the presence and the location of the one or more flaws may be stored using an electronic memory device. In some embodiments, the presence and the location of the one or more flaws may be projected onto a computer screen. According to some embodiments, the presence and the location of the one or more flaws may be projected onto the composite layup. In some embodiments, the algorithm used for determining the presence of one or more flaws may operate on the three dimensional point cloud.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicant reserves the right to file additional applications to pursue patents for subject matter that has been disclosed and enabled, but not claimed in the present application.

What is claimed is:

1. A system for detecting the presence and location of flaws in a composite layup material deposited on a mold by an automated fiber placement head, utilizing a three-dimensional point cloud representing a top surface of the composite layup material, comprising:
   a processing device;
   a laser line scanning device in communication with the processing device; and
   a non-transitory computer readable memory device in communication with the processing device, the non-transitory computer readable memory device storing instructions that when executed by the processing device result in:
      receiving, by the non-transitory computer readable memory device, programmed three-dimensional features of the top surface of the composite layup material, the top surface comprising a region of one or more courses of composite layup material;
      determining, by a scanning of the top surface conducted by the laser line scanning device, the three-dimensional point cloud representing the top surface of the composite layup material;
      receiving, from the laser line scanning device and by the processing device, information describing the three-dimensional point cloud representing the top surface of the composite layup material;
      determining, by the processing device and based on an analysis of the three-dimensional point cloud representing the top surface of the composite layup material, the analysis comprising an execution of a manufacturing flaw detection algorithm, a location of at least one manufacturing flaw on the top surface of the composite layup material;
      determining, by the processing device and based on an analysis of the three-dimensional point cloud representing the top surface of the composite layup material, the analysis comprising an execution of a feature detection algorithm, information descriptive of a location and a characteristic of one or more as-made features on the top surface of the composite layup material;
      comparing, by the processing device, the information descriptive of the location and the characteristic of the one of more as-made features on the top surface of the composite layup material with the programmed three-dimensional features of the top surface of the composite layup material;
      identifying by the processing device and based on the comparison and an execution of at least one as-made flaw detection algorithm, a presence and location of one or more as-made flaws on the top surface of the composite layup material;
      recording, by the non-transitory computer readable memory device, the presence and location of the one or more manufacturing flaws and the one or more as-made flaws on the top surface of the composite layup material; and
      causing, by the processing device and based on at least one of the locations of the one or more flaws on the top surface of the composite layup material, a repositioning of the automated fiber placement head,
   wherein the determining of the one or more as-made features of the top surface of the composite layup material comprises detecting a left tape edge location, a right tape edge location, a tape add location, a tape drop location, and a tape splice location,
   wherein the feature detection algorithm comprises a first module programmed to detect at least one of the left tape edge and the right tape edge, a second module programmed to detect at least one of the tape add location and the tape drop location, and a third module programmed to detect the tape splice location, and
   wherein the first module is programmed to detect the left tape edge, the three-dimensional point cloud comprises a set of data representing a plurality of scan lines oriented parallel to an x-axis, and wherein execution of the first module by the processing device results in:
      determining a subset of the three-dimensional point cloud representing the top surface of the composite layup material;
      determining positive slope peak locations along each scan line of the plurality of scan lines within the subset;
      locating proximate positive slope peak locations in proximate scan lines, thereby defining one or more positive slope peak point groups;
      calculating a mathematical fit correlation for each positive slope peak point group; and
      in the case that the mathematical fit correlation for a positive slope peak point group is above a predefined threshold, identifying the x-coordinate of the positive slope peak point group as the left tape edge.

2. The system of claim 1, wherein the subset of the three-dimensional point cloud representing the top surface of the composite layup material comprises a subset that is mathematically smoothed in the y-direction.

3. A system for detecting the presence and location of flaws in a composite layup material deposited on a mold by an automated fiber placement head, utilizing a three-dimensional point cloud representing a top surface of the composite layup material, comprising:
   a processing device;
   a laser line scanning device in communication with the processing device; and a non-transitory computer readable memory device in communication with the processing device, the non-transitory computer readable memory device storing instructions that when executed by the processing device result in:
  receiving, by the non-transitory computer readable memory device, programmed three-dimensional features of the top surface of the composite layup material, the top surface comprising a region of one or more courses of composite layup material;
  determining, by a scanning of the top surface conducted by the laser line scanning device, the three-dimensional point cloud representing the top surface of the composite layup material;
  receiving, from the laser line scanning device and by the processing device, information describing the three-dimensional point cloud representing the top surface of the composite layup material;
  determining, by the processing device and based on an analysis of the three-dimensional point cloud representing the top surface of the composite layup material, the analysis comprising an execution of a manufacturing flaw detection algorithm, a location of at least one manufacturing flaw on the top surface of the composite layup material;
  determining, by the processing device and based on an analysis of the three-dimensional point cloud representing the top surface of the composite layup material, the analysis comprising an execution of a feature detection algorithm, information descriptive of a location and a characteristic of one or more as-made features on the top surface of the composite layup material;
  comparing, by the processing device, the information descriptive of the location and the characteristic of the one of more as-made features on the top surface of the composite layup material with the programmed three-dimensional features of the top surface of the composite layup material;
  identifying by the processing device and based on the comparison and an execution of at least one as-made flaw detection algorithm, a presence and location of one or more as-made flaws on the top surface of the composite layup material;
  recording, by the non-transitory computer readable memory device, the presence and location of the one or more manufacturing flaws and the one or more as-made flaws on the top surface of the composite layup material; and
  causing, by the processing device and based on at least one of the locations of the one or more flaws on the top surface of the composite layup material, a repositioning of the automated fiber placement head,
  wherein the determining of the one or more as-made features of the top surface of the composite layup material comprises detecting a left tape edge location, a right tape edge location, a tape add location, a tape drop location, and a tape splice location,
  wherein the feature detection algorithm comprises a first module programmed to detect at least one of the left tape edge and the right tape edge, a second module programmed to detect at least one of the tape add location and the tape drop location, and a third module programmed to detect the tape splice location, and
  wherein the first module is programmed to detect the right tape edge, the three-dimensional point cloud comprises a set of data representing a plurality of scan lines oriented parallel to an x-axis, and wherein execution of the first module by the processing device results in:
    determining a subset of the three-dimensional point cloud representing the top surface of the composite layup material;
    determining negative slope peak locations along each scan line of the plurality of scan lines within the subset;
    locating proximate negative slope peak locations in proximate scan lines, thereby defining one or more negative slope peak point groups;
    calculating a mathematical fit correlation for each negative slope peak point group; and
    in the case that the mathematical fit correlation for a negative slope peak point group is above a predefined threshold, identifying the x-coordinate of the negative slope peak point group as the right tape edge.

4. The system of claim 3, wherein the subset of the three-dimensional point cloud representing the top surface of the composite layup material comprises a subset that is mathematically smoothed in the y-direction.

5. A system for detecting the presence and location of flaws in a composite layup material deposited on a mold by an automated fiber placement head, utilizing a three-dimensional point cloud representing a top surface of the composite layup material, comprising:
  a processing device;
  a laser line scanning device in communication with the processing device; and
  a non-transitory computer readable memory device in communication with the processing device, the non-transitory computer readable memory device storing instructions that when executed by the processing device result in:
    receiving, by the non-transitory computer readable memory device, programmed three-dimensional features of the top surface of the composite layup material, the top surface comprising a region of one or more courses of composite layup material;
    determining, by a scanning of the top surface conducted by the laser line scanning device, the three-dimensional point cloud representing the top surface of the composite layup material;
    receiving, from the laser line scanning device and by the processing device, information describing the three-dimensional point cloud representing the top surface of the composite layup material;
    determining, by the processing device and based on an analysis of the three-dimensional point cloud representing the top surface of the composite layup material, the analysis comprising an execution of a manufacturing flaw detection algorithm, a location of at least one manufacturing flaw on the top surface of the composite layup material;
    determining, by the processing device and based on an analysis of the three-dimensional point cloud representing the top surface of the composite layup material, the analysis comprising an execution of a feature detection algorithm, information descriptive of a location and a characteristic of one or more as-made features on the top surface of the composite layup material;
    comparing, by the processing device, the information descriptive of the location and the characteristic of the one of more as-made features on the top surface of the composite layup material with the programmed three-dimensional features of the top surface of the composite layup material;

identifying by the processing device and based on the comparison and an execution of at least one as-made flaw detection algorithm, a presence and location of one or more as-made flaws on the top surface of the composite layup material;

recording, by the non-transitory computer readable memory device, the presence and location of the one or more manufacturing flaws and the one or more as-made flaws on the top surface of the composite layup material; and causing, by the processing device and based on at least one of the locations of the one or more flaws on the top surface of the composite layup material, a repositioning of the automated fiber placement head, wherein the determining of the one or more as-made features of the top surface of the composite layup material comprises detecting a left tape edge location, a right tape edge location, a tape add location, a tape drop location, and a tape splice location, wherein the feature detection algorithm comprises a first module programmed to detect at least one of the left tape edge and the right tape edge, a second module programmed to detect at least one of the tape add location and the tape drop location, and a third module programmed to detect the tape splice location, and wherein the second module is programmed to detect the tape add location, the three-dimensional point cloud comprises a set of data representing a plurality of scan axis lines oriented parallel to a y-axis, and wherein execution of the second module by the processing device results in:

determining a subset of the three-dimensional point cloud representing the top surface of the composite layup material;

determining positive slope peak locations along each scan axis line of the plurality of scan axis lines within the subset;

locating proximate positive slope peak locations in proximate scan axis lines, thereby defining one or more positive slope peak point groups;

calculating a mathematical fit correlation for each positive slope peak point group; and in the case that the mathematical fit correlation for a positive slope peak point group is above a predefined threshold, identifying the y-coordinate of the positive slope peak point group as the tape add location.

6. The system of claim 5, wherein the subset of the three-dimensional point cloud representing the top surface of the composite layup material comprises a subset that is mathematically smoothed in the x-direction.

7. A system for detecting the presence and location of flaws in a composite layup material deposited on a mold by an automated fiber placement head, utilizing a three-dimensional point cloud representing a top surface of the composite layup material, comprising:

a processing device;

a laser line scanning device in communication with the processing device; and a non-transitory computer readable memory device in communication with the processing device, the non-transitory computer readable memory device storing instructions that when executed by the processing device result in:

receiving, by the non-transitory computer readable memory device, programmed three-dimensional features of the top surface of the composite layup material, the top surface comprising a region of one or more courses of composite layup material;

determining, by a scanning of the top surface conducted by the laser line scanning device, the three-dimensional point cloud representing the top surface of the composite layup material;

receiving, from the laser line scanning device and by the processing device, information describing the three-dimensional point cloud representing the top surface of the composite layup material;

determining, by the processing device and based on an analysis of the three-dimensional point cloud representing the top surface of the composite layup material, the analysis comprising an execution of a manufacturing flaw detection algorithm, a location of at least one manufacturing flaw on the top surface of the composite layup material;

determining, by the processing device and based on an analysis of the three-dimensional point cloud representing the top surface of the composite layup material, the analysis comprising an execution of a feature detection algorithm, information descriptive of a location and a characteristic of one or more as-made features on the top surface of the composite layup material;

comparing, by the processing device, the information descriptive of the location and the characteristic of the one of more as-made features on the top surface of the composite layup material with the programmed three-dimensional features of the top surface of the composite layup material;

identifying by the processing device and based on the comparison and an execution of at least one as-made flaw detection algorithm, a presence and location of one or more as-made flaws on the top surface of the composite layup material;

recording, by the non-transitory computer readable memory device, the presence and location of the one or more manufacturing flaws and the one or more as-made flaws on the top surface of the composite layup material; and causing, by the processing device and based on at least one of the locations of the one or more flaws on the top surface of the composite layup material, a repositioning of the automated fiber placement head, wherein the determining of the one or more as-made features of the top surface of the composite layup material comprises detecting a left tape edge location, a right tape edge location, a tape add location, a tape drop location, and a tape splice location, wherein the feature detection algorithm comprises a first module programmed to detect at least one of the left tape edge and the right tape edge, a second module programmed to detect at least one of the tape add location and the tape drop location, and a third module programmed to detect the tape splice location, and wherein the second module is programmed to detect the tape drop location, the three-dimensional point cloud comprises a set of data representing a plurality of scan axis lines oriented parallel to a y-axis, and wherein execution of the second module by the processing device results in:
  determining a subset of the three-dimensional point cloud representing the top surface of the composite layup material;
  determining negative slope peak locations along each scan axis line of the plurality of scan axis lines within the subset;
  locating proximate negative slope peak locations in proximate scan axis lines, thereby defining one or more negative slope peak point groups;
  calculating a mathematical fit correlation for each negative slope peak point group; and
  in the case that the mathematical fit correlation for a negative slope peak point group is above a predefined threshold, identifying the y-coordinate of the negative slope peak point group as the tape drop location.

8. The system of claim 7, wherein the subset of the three-dimensional point cloud representing the top surface of the composite layup material comprises a subset that is mathematically smoothed in the x-direction.

9. A system for detecting the presence and location of flaws in a composite layup material deposited on a mold by an automated fiber placement head, utilizing a three-dimensional point cloud representing a top surface of the composite layup material, comprising:
  a processing device;
  a laser line scanning device in communication with the processing device; and
  a non-transitory computer readable memory device in communication with the processing device, the non-transitory computer readable memory device storing instructions that when executed by the processing device result in:
    receiving, by the non-transitory computer readable memory device, programmed three-dimensional features of the top surface of the composite layup material, the top surface comprising a region of one or more courses of composite layup material;
    determining, by a scanning of the top surface conducted by the laser line scanning device, the three-dimensional point cloud representing the top surface of the composite layup material;
    receiving, from the laser line scanning device and by the processing device, information describing the three-dimensional point cloud representing the top surface of the composite layup material;
    determining, by the processing device and based on an analysis of the three-dimensional point cloud representing the top surface of the composite layup material, the analysis comprising an execution of a manufacturing flaw detection algorithm, a location of at least one manufacturing flaw on the top surface of the composite layup material;
    determining, by the processing device and based on an analysis of the three-dimensional point cloud representing the top surface of the composite layup material, the analysis comprising an execution of a feature detection algorithm, information descriptive of a location and a characteristic of one or more as-made features on the top surface of the composite layup material;
    comparing, by the processing device, the information descriptive of the location and the characteristic of the one of more as-made features on the top surface of the composite layup material with the programmed three-dimensional features of the top surface of the composite layup material;
    identifying by the processing device and based on the comparison and an execution of at least one as-made flaw detection algorithm, a presence and location of one or more as-made flaws on the top surface of the composite layup material;
    recording, by the non-transitory computer readable memory device, the presence and location of the one or more manufacturing flaws and the one or more as-made flaws on the top surface of the composite layup material; and
    causing, by the processing device and based on at least one of the locations of the one or more flaws on the top surface of the composite layup material, a repositioning of the automated fiber placement head,
  wherein the determining of the one or more as-made features of the top surface of the composite layup material comprises detecting a left tape edge location, a right tape edge location, a tape add location, a tape drop location, and a tape splice location,
  wherein the feature detection algorithm comprises a first module programmed to detect at least one of the left tape edge and the right tape edge, a second module programmed to detect at least one of the tape add location and the tape drop location, and a third module programmed to detect the tape splice location, and
  wherein the third module is programmed to detect the tape splice location, the tape splice location comprises a splice add location and a splice drop location, and wherein execution of the third module by the processing device results in:
    determining each tape add location for a particular scan axis line;
    determining each tape drop location for the particular scan axis line;
    subtracting, for each consecutive tape add location and tape drop location, the y-coordinate of the tape add location from the y-coordinate of the tape drop location, thereby determining a tape segment length; and
    comparing the tape segment length to a predetermined splice length threshold;
    determining, based on the comparing of the tape segment length to the predetermined splice length threshold, that the tape segment is within the predetermined splice length threshold; and
    identifying, based on the determining that the tape segment is within the predetermined splice length threshold, that the consecutive tape add location and tape drop location are the splice add location and the splice drop location, respectively.

10. The system of claim 9, wherein the causing of the repositioning of the automated fiber placement head, comprises:
  transmitting, by the processing device and to an automated fiber placement machine, a command that causes the automated fiber placement machine to actuate a robotic positioning device to reposition the automated fiber placement head to a location on the composite layup material surface at which at least one of the flaws of the composite layup surface material was identified.

11. The system of claim 9, wherein the execution of the instructions by the processing device further results in:

processing the three-dimensional point cloud representing the top surface of the composite layup material by interpolating missing points in the point cloud and smoothing the point cloud.

12. The system of claim 9, wherein the execution of the instructions by the processing device further results in:
projecting data descriptive of a location of one or more of the flaws of the composite layup material top surface onto the composite layup material top surface.

13. The system of claim 1, wherein the causing of the repositioning of the automated fiber placement head, comprises:
transmitting, by the processing device and to an automated fiber placement machine, a command that causes the automated fiber placement machine to actuate a robotic positioning device to reposition the automated fiber placement head to a location on the composite layup material surface at which at least one of the flaws of the composite layup surface material was identified.

14. The system of claim 1, wherein the execution of the instructions by the processing device further results in:
processing the three-dimensional point cloud representing the top surface of the composite layup material by interpolating missing points in the point cloud and smoothing the point cloud.

15. The system of claim 3, wherein the causing of the repositioning of the automated fiber placement head, comprises:
transmitting, by the processing device and to an automated fiber placement machine, a command that causes the automated fiber placement machine to actuate a robotic positioning device to reposition the automated fiber placement head to a location on the composite layup material surface at which at least one of the flaws of the composite layup surface material was identified.

16. The system of claim 3, wherein the execution of the instructions by the processing device further results in:
processing the three-dimensional point cloud representing the top surface of the composite layup material by interpolating missing points in the point cloud and smoothing the point cloud.

17. The system of claim 5, wherein the causing of the repositioning of the automated fiber placement head, comprises:
transmitting, by the processing device and to an automated fiber placement machine, a command that causes the automated fiber placement machine to actuate a robotic positioning device to reposition the automated fiber placement head to a location on the composite layup material surface at which at least one of the flaws of the composite layup surface material was identified.

18. The system of claim 5, wherein the execution of the instructions by the processing device further results in:
processing the three-dimensional point cloud representing the top surface of the composite layup material by interpolating missing points in the point cloud and smoothing the point cloud.

19. The system of claim 7, wherein the causing of the repositioning of the automated fiber placement head, comprises:
transmitting, by the processing device and to an automated fiber placement machine, a command that causes the automated fiber placement machine to actuate a robotic positioning device to reposition the automated fiber placement head to a location on the composite layup material surface at which at least one of the flaws of the composite layup surface material was identified.

20. The system of claim 7, wherein the execution of the instructions by the processing device further results in:
processing the three-dimensional point cloud representing the top surface of the composite layup material by interpolating missing points in the point cloud and smoothing the point cloud.

21. The system of claim 1, wherein the execution of the instructions by the processing device further results in:
projecting data descriptive of a location of one or more of the flaws of the composite layup material top surface onto the composite layup material top surface.

22. The system of claim 3, wherein the execution of the instructions by the processing device further results in:
projecting data descriptive of a location of one or more of the flaws of the composite layup material top surface onto the composite layup material top surface.

23. The system of claim 5, wherein the execution of the instructions by the processing device further results in:
projecting data descriptive of a location of one or more of the flaws of the composite layup material top surface onto the composite layup material top surface.

24. The system of claim 7, wherein the execution of the instructions by the processing device further results in:
projecting data descriptive of a location of one or more of the flaws of the composite layup material top surface onto the composite layup material top surface.

* * * * *